United States Patent
Bech et al.

(10) Patent No.: US 6,932,893 B2
(45) Date of Patent: Aug. 23, 2005

(54) SYSTEM FOR ELECTROPHYSIOLOGICAL MEASUREMENTS

(75) Inventors: Morten Bech, Holte (DK); Jørgen Due, Ølstykke (DK); Lars Thomsen, Aalborg Ø (DK); Jonatan Kutchinsky, Frederiksberg C (DK); Rafael Taboryski, Lyngby (DK); Bent Erling Nielsen, Lyngby (DK); John Shaw, West Drayton (GB); John Dodgson, Croydon (GB)

(73) Assignee: Sophion Bioscience A/S, Ballerup (DK)

( * ) Notice: Subject to any disclaimer, the term of this patent is extended or adjusted under 35 U.S.C. 154(b) by 234 days.

(21) Appl. No.: 09/967,932

(22) Filed: Oct. 2, 2001

(65) Prior Publication Data

US 2002/0063067 A1 May 30, 2002

Related U.S. Application Data

(60) Provisional application No. 60/267,708, filed on Feb. 12, 2001, and provisional application No. 60/238,449, filed on Oct. 10, 2000.

(30) Foreign Application Priority Data

Oct. 2, 2000 (DK) ........................................ 2000 01458
Feb. 9, 2001 (DK) ........................................ 2001 00212

(51) Int. Cl.[7] ........................ G01N 33/487; C12M 1/34
(52) U.S. Cl. ............... 204/403.01; 204/406; 435/287.1; 435/288.5
(58) Field of Search ...................... 204/403.01, 406; 435/287.1, 288.4, 288.5

(56) References Cited

U.S. PATENT DOCUMENTS 4,510,442 A * 4/1985 Neher ...................... 324/99 R
5,187,096 A    2/1993 Giaever et al.
6,315,940 B1  11/2001 Nisch et al.
6,488,829 B1 * 12/2002 Schroeder et al. ..... 204/403.01
6,699,697 B2 *  3/2004 Klemic et al. ........... 435/173.4

FOREIGN PATENT DOCUMENTS

| WO | WO 98/54294 | 12/1998 |
| WO | WO 99/31503 | 6/1999 |
| WO | WO 99/66329 | 12/1999 |
| WO | WO 01/27614 A1 | 4/2001 |
| WO | WO 01/48474 A1 | 5/2001 |
| WO | WO 01/25769 A2 | 12/2001 |

OTHER PUBLICATIONS

The Axon Guide for Electrophysiology & Biophysics Laboratory Techniques, Jun. 1993.*
Provisional application 60/181,935, filed on Feb. 11, 2000.*
E. Neher et al., *Pflügers Arch.*, 375, 219–228 (1978).
O. P. Hamill et al., *Pflügers Arch.*, (1981) 391:85–100.

* cited by examiner

Primary Examiner—Kaj K. Olsen
(74) Attorney, Agent, or Firm—Birch, Stewart, Kolasch & Birch, LLP

(57) ABSTRACT

The present invention relates to a high through-put system for determining and/or monitoring electrophysiological properties of ion channels of ion channel-containing membranes, typically lipid membrane-containing structures such as cells. In particular, the invention provides a substrate which provides means for automatically positioning cells at measuring sites using electroosmotic flow in canals formed on or in the substrate. The electroosmotic flow is generated and controlled by electroosmotic flow pumps integrated on the substrate or positioned in relation thereto. Thereby, cells can be positioned in favorable measurement configuration at a plurality of sites for performing testing and measurements. Also, the invention relates to a main electric circuit for performing testing and measurements on a plurality of cells in parallel.

6 Claims, 21 Drawing Sheets

$R_{series} = R_{membrane} + R_{acces}$ $C_{slow} = C_{membrane}$ $C_{fast} = C_{acces}$

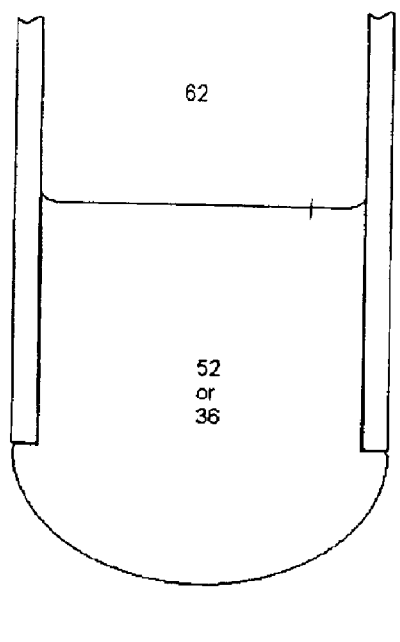
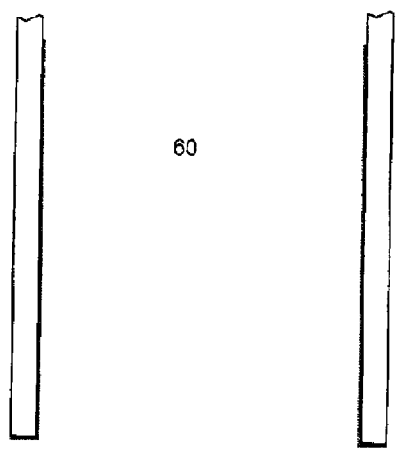
Fig. 24A
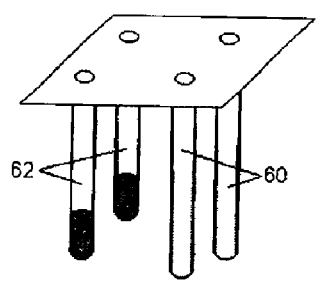
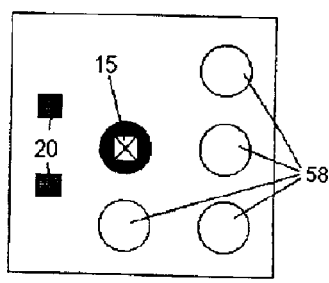
Fig. 24B        Fig. 24C

SYSTEM FOR ELECTROPHYSIOLOGICAL MEASUREMENTS

This nonprovisional application claims priority under 35 U.S.C. §119(e) on U.S. Provisional Application Nos. 60/238,449 and 60/267,708 filed on Oct. 10, 2000 and Feb. 12, 2001, respectively, which are herein incorporated by reference.

FIELD OF THE INVENTION

The present invention relates to a high throughput system for determining and/or monitoring electrophysiological properties of ion channels of ion channel-containing membranes, typically lipid membrane-containing structures such as cells. The system provides means for performing an automated process including preparation of the cells, preparation of the measuring configuration, and performing the measurements on a large number of cells independently. Also, the invention relates to a substrate and a method for establishing an electrophysiological measuring configuration in which a cell membrane forms a high resistive seal in a configuration with measuring electrodes, making it possible to determine and monitor a current flow through the cell membrane. More particularly, the invention relates to such a substrate which provides means for automatically positioning cells at measuring sites using electroosmotic flow. Also, the invention relates to a main electric circuit for performing testing and measurements on cells at a plurality of sites in parallel.

BACKGROUND OF THE INVENTION

The general idea of electrically isolating a patch of membrane and studying the ion channels in that patch under voltage-clamp conditions was outlined by Neher, Sakmann, and Steinback in "The Extracellular Patch Clamp, A Method For Resolving Currents Through Individual Open Channels In Biological Membranes", Pflueger Arch. 375; 219–278, 1978. They found that, by pressing a pipette containing acetylcholine (ACh) against the surface of a muscle cell membrane, they could see discrete jumps in electrical current that were attributable to the opening and closing of ACh-activated ion channels. However, they were limited in their work by the fact that the resistance of the seal between the glass of the pipette and the membrane (10–50 MΩ) was very small relative to the resistance of the channel (10 GΩ). The electrical noise resulting from such a seal is inversely related to the resistance and was large enough to obscure the currents flowing through ion channels, the conductance of which are smaller than that of the ACh channel. It also prohibited the clamping of the voltage in the pipette to values different from that of the bath due to the large currents through the seal that would result.

It was then discovered that by fire polishing the glass pipettes and by applying suction to the interior of the pipette a seal of very high resistance (1–100 GΩ) could be obtained with the surface of the cell. This giga-seal reduced the noise by an order of magnitude to levels at which most channels of biological interest can be studied and greatly extended the voltage range over which these studies could be made. This improved seal has been termed a "giga-seal", and the pipette has been termed a "patch pipette". A more detailed description of the giga-seal may be found in O.P. Hamill, A. Marty, E. Neher, B. Sakmann & F. J. Sigworth: Improved patch-clamp techniques for high resolution current recordings from cells and cell-free membrane patches. Pflügers Arch. 391, 85–100, 1981. For their work in developing the patch clamp technique, Neher and Sakmann were awarded the 1991 Nobel Prize in Physiology and Medicine.

Ion channels are transmembrane proteins which catalyse transport of inorganic ions across cell membranes. The ion channels participate in processes as diverse as generating and timing action potentials, synaptic transmission, secretion of hormones, contraction of muscles, etc. Many drugs exert their specific effects via modulation of ion channels. Examples are antiepileptic compounds like phenytoin and lamotrigine which block voltage-dependent $Na^+$-channels in the brain, antihypertensive drugs like nifedipine and diltiazem which block voltage dependent $Ca^{2+}$-channels in smooth muscle cells, and stimulators of insulin release like glibenclamide and tolbutamide which block an ATP-regulated $K^+$-channel in the pancreas. In addition to chemically induced modulation of ion-channel activity, the patch clamp technique has enabled scientists to perform manipulations with voltage dependent channels. These techniques include adjusting the polarity of the electrode in the patch pipette and altering the saline composition to moderate the free ion levels in the bath solution.

The patch clamp technique represents a major development in biology and medicine, since this technique allows measurement of ion flow through single ion channel proteins, and also allows the study of the single ion channel responses to drugs. Briefly, in standard patch clamp technique, a thin (app. 0.5–2 $\mu$m in diameter) glass pipette is used. The tip of this patch pipette is pressed against the surface of the cell membrane. The pipette tip seals tightly to the cell and isolates a few ion channel proteins in a tiny patch of membrane. The activity of these channels can be measured individually (single channel recording) or, alternatively, the patch can be ruptured, allowing measurements of the channel activity of the entire cell membrane (whole-cell configuration). High-conductance access to the cell interior for performing whole-cell measurements can be obtained by rupturing the membrane by applying negative pressure in the pipette.

During both single channel recording and whole-cell recording, the activity of individual channel subtypes can be characterised by imposing a "voltage clamp" across the membrane. In the voltage clamp technique the membrane current is recorded at a constant membrane potential. Or—to be more precise—the amplifier supplies exactly the current which is necessary to keep the membrane potential at a level determined by the experimenter. Hence, currents resulting from opening and closing of ion channels are not allowed to recharge the membrane.

A major limitation determining the throughput of the patch clamp technique is localisation and clamping of cells and pipette, and the nature of the feeding system, which leads the dissolved compound to cells and patches. In usual patch clamp setups, cells are placed in experimental chambers, which are continuously perfused with a physiological salt solution. The establishment of the cell-pipette connection in these chambers is time consuming and troublesome. Compounds are applied by changing the inlet to a valve connected to a small number of feeding bottles. The required volumes of the supporting liquid and the compound to be tested are high.

High throughput systems for performing patch clamp measurements have been proposed, which typically consist of a substrate with a plurality of sites adapted to hold cells in a measuring configuration where the electrical properties of the cell membrane can be determined.

U.S. Pat No. 5,187,096, Rensselaer, discloses an apparatus for monitoring cell-substrate impedance of cells. Cells are cultured directly on the electrodes which are then covered with a plurality of cells, thus, measurements on individual cells can not be performed.

WO 98/54294, Leland Stanford, discloses a substrate with wells containing electrode arrays. The substrate with wells and electrodes are formed in silicon using CVD (Chemical Vapor Deposition) and etching techniques and comprises Silicon Nitride "passivation" layers surrounding the electrodes. Cells are cultivated directly on the electrode array. The substrate is adapted to measure electrophysiological properties and discloses a variety of proposed measuring schemes.

WO 99/66329, Cenes, discloses a substrate with perforations arranged in wells and electrodes provided on each side of the substrate. The substrate is formed by perforating a silicon substrate with a laser and may be coated with anti-adhesive material on the surface. The substrate is adapted to establish giga-seals with the cells by positioning the cells on the perforations using suction creating a liquid flow through the perforations, providing the anti-adhesion layer surrounding the perforations, or by guiding the cells electrically. The cells can be permeabilised by EM fields or chemical methods in order to provide a whole-cell-measuring configuration. All perforations, and hence all measurable cells, in a well shares one working electrode and one reference electrode, see FIG. 11, hence measurements on individual cells can not be performed.

WO 99/31503, Vogel et al., discloses a measuring device with a passage arranged in a well on a substrate (carrier) and separating two compartments. The measuring device comprises two electrodes positioned on either side of the passage and adapted to position a cell at the passage opening. The substrate may have hydrophobic and hydrophilic regions in order to guide the positioning of the cells at the passage opening.

SUMMARY OF THE INVENTION

The state of the art is focused on the detailed fabrication and design of the substrates containing electrodes, wells, perforations etc. and on the methods of establishment of an applicable measuring configuration. This is very natural, since the changes of the known patch clamp devices are the replacement of the pipette with the substrate and the manual localisation of cells with the automatic positioning of cells. However, although these aspects represent important steps on the way to providing an automatic patch clamp apparatus, a number of problems are left unconsidered.

According to the present invention, an ion channel-containing lipid membrane may be positioned at a site by using an electrical field to generate an electroosmotic flow in a canal with an ionic solution containing the ion channel-containing lipid membrane. In order to create the electroosmotic flow, the geometry as well as the materials of the canal has to be carefully chosen. Holding the ion channel-containing lipid membrane in the ionic solution, or using the flow in the ionic solution to generate a flow in a liquid containing ion channel-containing lipid membranes, the ion channel-containing lipid membranes may be directed to a desired position.

Hence, in a first aspect, the present invention provides a substrate for determination and/or monitoring of electrophysiological properties of ion channels in ion channel-containing lipid membranes, said substrate comprising:

a first site for holding ion channel-containing lipid membranes, the site comprising a passage in the substrate, a first end of the passage being in contact with a first domain at a first upper surface part of the substrate and a second end of the passage being in contact with a second domain in a first canal, a reference electrode in electrical contact with the first domain, a working electrode in electrical contact with the second domain, one or more electrodes for generating a first electrical field in the first canal, the further electrodes having dimensions and positions so as for the first electrical field to induce a flow in an ionic solution held in the first canal, the second end of the passage and the first canal being dimensioned so that a flow of an ionic solution in the first canal can generate a flow through the passage from the first domain into the second domain or vice versa, and the first end part of the passage being adapted to form a seal with an ion channel-containing lipid membrane held at the site, the substrate, the seal and the lipid membrane thereby separating the first domain of the site from the second domain so that one or more electrical properties of the membrane can be determined and/or monitored by determining and/or monitoring an electrical signal between the reference electrode and the working electrode.

Preferably, the dimensions and material composition of the first end parts of the passages are adapted to provide high electrical resistance seals between an ion channel-containing lipid membrane held at a site and the substrate. In the present context, a high electrical resistance seal means that the electrical resistance along a path between the adjoining surfaces of the substrate and the membrane is of the order of 10 M$\Omega$ or larger, preferably larger than 100 M$\Omega$ or 1 G$\Omega$, also known as a giga seal.

The canal may be formed in the substrate or consist of a groove formed in a surface part of the substrate which is subsequently closed by arranging another substrate on said surface part thereby forming a canal or pipe. Electroosmotic flow is generated by application of an electric field through a solution in a channel defined by insulating walls. The phenomenon depends on ionisation of the surface so that for electroneutrality there is an excess mobile charge in the solution, located close to the walls within a thin screening layer. An electric field applied to the solution acts on the excess charge in the solution causing the fluid to flow. The quantity and distribution of excess charge in the solution depends on the surface material (density of ionisable sites) and on the solution composition, especially pH and ionic concentration. From the charge distribution a single parameter, the zeta ($\zeta$) potential, can be extracted, which determines the strength of the electroosmotic flow. However, although values for the zeta potential are measured and published for material/solution combinations it is not really a readily controllable parameter, and as it arises from the ionisation of surface sites, $\zeta$ and EOF are very susceptible to changes in surface condition and contamination. Preferably, the sidewalls of at least part of the first canal are formed by a material having an effective zeta ($\zeta$) potential larger than or equal to 10 mV. Examples of such materials are silica or glass.

The substrate may comprise further sites with passages having end parts in contact with the first and second domains. Thus, more than one site may share the first canal whereby the flow generated in the first canal can be used to control a flow in several passages in parallel.

The substrate preferably further comprises a first end part to the canal for introduction of an ionic solution in the canal.

In order for the electric field to efficiently induce a flow in the ionic solution, the ionic solution should be in electrical contact with at least two of the electrodes in contact with the second domain. It would therefore be preferred that an ionic solution, when introduced in the canal, automatically establishes electrical contact with the electrodes in contact with the second domain. Hence, the dimensions of the canal and the first end part of the canal as well as the dimensions and positions of the electrodes in contact with the second domain are preferably adapted so as for an ionic solution introduced through the first end part to form electrical contact with the electrodes in contact with the second domain. In order to assist introduction of an ionic solution in to the canal, the substrate may further comprise one or more regions of hydrophilic or hydrophobic material arranged in relation to the canal, in the canal, or in the first end part of the canal.

In a preferred embodiment, the substrate comprises a second end part to the canal, wherein the first and the second end part to the canal constitutes an inlet and an outlet to the canal at a second upper surface part of the substrate. In this embodiment, a first of the electrodes in contact with the second domain may be positioned either in the passage or at the second end of the passage and a second electrode is positioned closer to the first end part of the canal than the first, also the substrate may further comprise a third electrode positioned closer to the second end part of the canal than the first electrode. Thereby, a configuration is obtained where the working electrode is positioned in a central part of the canal and the second and third electrodes are positioned in opposite ends of the canal. If e.g. the second and third electrodes are kept at substantially the same electrical potential and the first electrode is held at a lower electrical potential, a flow is induced from both end parts towards the first electrode, whereby a high pressure may efficiently be build at the position of the aperture. If, on the other hand, the first electrode is held at a higher electrical potential than the second and third electrodes, a flow is induced from the first electrode towards both end parts, whereby a low pressure may efficiently be build at the position of the aperture. Any of the electrodes may also function as the working electrode.

In another preferred embodiment, the first end part to the canal constitutes an inlet or an outlet to the canal at a second upper surface part of the substrate, whereas a second end part to the canal is constituted by the passage.

In still another preferred embodiment, the substrate comprises a second canal in contact with the first domain and the upper end part of the passage, the second canal having a first and a second end, and two or more electrodes in contact with the first domain for generating a first electrical field in the second canal, the further electrodes having dimensions and positions so as for the first electrical field to induce a flow in an ionic solution held in the second canal, the site and the second canal being dimensioned so that a flow of an ionic solution in the second canal can generate a flow from the first end of the second canal to the second end past the site. Preferably, the substrate may further comprise detection means, e.g. a Coulter counter principle or equivalent, for determining when an ion channel-containing lipid membrane contained in the ionic solution in the second canal is in the vicinity of the site and means for controlling the flow in the second canal in response to signals from said detection means.

The electroosmotic flow in the first (and second) canal is generated by an electroosmotic flow pump (EOF pump), being a particular design and configuration of at least part of the canal and the electrodes for generating the electric field. The EOF pump may be integrated on the substrate by forming the first/second canal and the electrodes in/on the substrate. Alternatively, the EOF pump may be formed on another substrate or structure in a canal brought into contact with the first/second canal before application to establish a flow in the first/second canal by the EOF pump not held by the substrate. Thereby, the substrate holding the cell and the compounds to be tested may be disposable whereas the EOF pumps and related electronics can be used repetitively.

The passage, which has its first end part within the site, preferably has a transverse dimension of at the most $10\ \mu m$, preferably in the range of $0.5-5\ \mu m$. Also, an interior surface defined by the passage of the site may carry a substance, such as sodium chloride, which will contribute to draw an aqueous liquid which is in contact with the substrate at an end of the passage into and through the passage.

A reference electrode may be shaped so as to, when projected onto a plane comprising a passage in contact with a first domain in contact with the reference electrode, at least partly encircle said passage. In this scheme, the working electrode is preferably positioned in or near the second end of the passage. This shape of the reference electrode serves to, when an electric potential is applied between the reference and the working electrode, generate an electric field with field lines converging at the first end of the passage, which field will exert a force on an ion channel-containing lipid membrane, guiding it towards the first end of the passage.

In a second aspect, the present invention provides a method for establishing a measuring configuration for measuring electrophysiological properties of ion channels in ion channel-containing lipid membranes, said method comprising the steps of:

providing a substrate having a first site for holding ion channel-containing lipid membranes, the site comprising a passage in the substrate, a first end of the passage being in contact with a first domain at a first upper surface part of the substrate and a second end of the passage being in contact with a second domain in a first canal below said first upper surface part of the substrate, providing a reference electrode at the first upper surface part of the substrate, the reference electrode being in electrical contact with the first domain, providing two or more electrodes being in electrical contact with the second domain, one of which is a working electrode, supplying a carrier liquid in the first domain, supplying an ionic solution in the second domain, the ionic solution being in electrical contact with at least one of the electrodes, and forming an electrical field in the first canal by applying an electric potential difference between at least two of the electrodes in electrical contact with the second domain, said electrical field traversing the second domain so as to generate a flow in the ionic solution in the first canal whereby a liquid flow from the first domain into the second domain, or from the second domain into the first domain, is generated.

Preferably, the carrier liquid supplied in the first domain comprises one or more ion channel-containing lipid membranes, and the electric field generates a liquid flow from the first domain into the second domain until an ion channel-containing lipid membrane seals to the first end of the passage and separate the first domain of the site from the second domain.

According to the method of the second aspect, the electrical potential applied between the electrodes generating the flow may be at least substantially constant so as to provide an at least substantially constant magnitude of the electrical field, disregarding the induced flow in the ionic solution. According to such scheme, the maximum strength of the electrical field may be in the interval $10$–$10^6$ Volt/centimeter. The applied value depends to a large degree on the design and dimensions of the EOF pump.

Alternatively, the electrical potential applied between the electrodes generating the flow may be adjusted so as to generate an at least substantially constant electrical current between the electrodes. According to such scheme, the strength of the electrical current between the electrodes generating the flow may be in the interval 0.1–10000 $\mu A$.

In another alternative, the electrical potential applied between the electrodes generating the flow may be adjusted so as to maintain an at least substantially constant flow in the canal. The at least substantially constant flow being determined with regard to the dimensions of the canal and the passage.

Preferably, the step of supplying an ionic solution in the second domain comprises the step of supplying the ionic liquid to an inlet to the canal at a second upper surface part of the substrate.

In order to assist in the positioning of a cell at a site, the method may comprise the steps of providing a second canal in contact with the first domain and the upper end part of the passage, the second canal having a first and a second end, and generating a first electrical field in the second canal to induce a flow from the first end of the second canal to the second end past the site in an ionic solution held in the second canal. Thus, an electroosmotic flow may be generated in a canal in the first domain in order to lead the cells to the upper end of the passage. Preferably, the method may further comprise the step of determining when an ion channel-containing lipid membrane contained in the ionic solution in the second canal is in the vicinity of the site and controlling the flow in the second canal in response to said determination.

Preferably, the ion channel-containing lipid membrane forms a high electrical resistance seal, such as a giga-seal, with the first end of the passage so that one or more electrical properties of the membrane can be determined and/or monitored by determining and/or monitoring an electrical signal between the electrodes generating the flow.

After establishment of the high electrical resistance seal, the method preferably comprises the step of checking the high electrical resistance seal between an ion channel-containing membrane held at a site and the first end of the passage by successively applying a first electric potential difference between the working electrode and the reference electrode and monitoring a first current flowing between the working electrode and the reference electrode. If the first current is smaller than or equal to a predetermined threshold current, then the site may be approved as having an acceptable seal between the ion cannel-containing structure and the first end of the passage. This method step is used to determine the character of the established seal. If there is no giga-seal, then a large leak current will flow between the membrane and the site. If a giga-seal is established, the current is primarily drawn through the membrane and will be significantly smaller than the leak current.

Also, after establishment of the high electrical resistance seal, the method preferably comprises the step of establishing a whole-cell configuration by rupturing the part of the ion channel-containing membrane which is closest to the working electrode. The rupturing of the part of the membrane may be performed by applying a series of second electric potential difference pulses between the working electrode and the reference electrode. The rupture of the membrane may be determined by monitoring a current flowing between the working electrode and the reference electrode, when this current exceeds a predetermined threshold value, the membrane has been ruptured and the series of second electric potential difference pulses may be interrupted. Preferably, the series of second electric potential difference pulses consist of a series of voltage step functions of increasing amplitude and/or duration. When the membrane is ruptured due to the strong electric field, a capacitative spike will appear in the resulting current response.

Alternatively, the rupturing may be performed by forming a negative hydrostatic pressure in the passage by applying an electric potential difference between the electrodes generating the electroosmotic flow, said electrical field traversing the second domain so as to generate a flow in the ionic solution in the canal whereby a suction to a part of the ion channel-containing lipid membrane covering the first end of the passage is generated, until said part of the ion channel-containing lipid membrane is ruptured. Also, by providing a pore forming compound in the passage, a part of the ion channel-containing membrane which is in accessible from the passage may be permeabilised.

In the present context, when a reference electrode is said to at least partly encircle a passage or a working electrode, it is meant that the reference electrode has a shape forming, in said plane, a region which is surrounded by the reference electrode, which region is free of reference electrode and which holds the passage or the working electrode. Thus, the reference electrode forms an open or closed ring in said plane, within which ring the passage or the working electrode is positioned. The reference can not cover the passage or the working electrode even though parts of the reference electrode would in this case surround the passage or the working electrode. In other words, if straight lines are drawn between an inner perimeter of the reference electrode to an outer perimeter of the passage or the working electrode, then these lines should converge at the passage or the working electrode.

By forming an electrical field by applying an electrical potential difference between a working electrode and a reference electrode corresponding to said first domain or said site, the field lines from said electrical field increasing in density in a direction from the reference electrode to the working electrode, an ion channel-containing lipid membrane can be moved electrophoretically towards the working electrode and be positioned at the site and thereby separating the first domain of the site from the second domain.

Preferably, the shape of the one or more reference electrodes is at least substantially circular or rectangular. The circle or rectangle may be closed or have one or more minor openings.

In a preferred embodiment, the reference electrodes and/or the working electrodes comprises an electrode part covered with a first material layer forming an electrochemical bridge between the electrode part and the first and/or second domain. In this preferred embodiment, the reference and/or the working electrode may be a silver/silver halide electrode. Also, the reference electrode may be common to two or more sites.

In order to positioning, test, stimulate, measure, etc. on a large number of sites and cells (a large number of measuring channels) with a high throughput, the present invention provides a main electrical circuit for managing and performing the testing, stimulation, and measurements of a plurality of channels, which is not simply a plurality of single channel electrical circuits arranged in parallel. In order to provide a compact and cost-efficient main electrical circuit which can easily be managed by e.g. a computer, it is necessary to control the performance of the channels so that some components can be shared by a large number of channels.

Thus, in a third aspect, the present invention provides a system for determination and/or monitoring of electrophysiological properties of ion channels in ion channel-containing lipid membranes, the system comprising a substrate comprising a plurality of sites for holding ion channel-containing lipid membranes, a plurality of working electrodes (6), one working electrode positioned at each site, and one or more reference electrodes (8) positioned so as for each site to be in electrical contact with at least one reference electrode, each site being adapted to hold an ion channel-containing lipid membrane so as for an electrical current $I_{mem}$ drawn between the working electrode of a site and a reference electrode will be transmitted by ion channels in the ion channel-containing lipid membrane, the system further comprising a main electric circuit for performing voltage clamp measurements on ion channel-containing lipid membranes held at the sites, said main electric circuit comprising

- a plurality of current to voltage (I-V) converters each having a first and a second input and an output, the first input being electrically connected to a working electrode and the second input receiving a reference potential $V_{ref}$, each I-V converter being adapted to, upon receiving the reference potential $V_{ref}$, draw a current $I_{mem}$ between a reference electrode and the working electrode until the potential on the first input at least substantially equals $V_{ref}$, each I-V converter further being adapted to provide on its output a first voltage signal corresponding to $I_{mem}$,
- a first multiplexer having a plurality of inputs for receiving first voltage signals from two or more I-V converters and individually feeding the selected first voltage signals to a first A/D converter in a controlled manner, said first A/D converter to generate digital signals corresponding to the first voltage signals,
- a plurality of individually controllable switches, each being operationally connected to a working electrode and the multiplexer, for switching the first voltage signal to the multiplexer on or off,
- digital processing means for receiving and processing the digital signals, the digital processing means being adapted to administer and generate a first type of digital signals related to stimulation or testing of the ion channel-containing lipid membranes, the digital processing means further being adapted to administer and generate a second type of digital signals controlling individually controllable components of the main circuit,
- means for receiving the digital signals of the first type and for generating an analogue stimulation or testing signal $V_{stim}$ to be added to each $V_{ref}$,
- means for providing $V_{ref}$ to each I-V converter, each $V_{ref}$ being individually controllable, said means further being adapted to receive $V_{stim}$ and add $V_{stim}$ to one or more selected $V_{ref}$'s, and
- an enable network for receiving the digital signals of the second type from the digital processing means and for controlling:
  - the plurality of individually controllable switches,
  - the selection of the plurality of first voltage signals in the multiplexer,
  - the value of individual $V_{ref}$'s by controlling the means for providing $V_{ref}$, in response to the digital signals of the second type.

The digital processing means may be a DSP or a CPU. Alternatively, the digital processing means may form part of a larger processing means performing a number of additional functions such as data handling and storage, interfacing with other units in the system, etc.

Preferably, the individually controllable switches and/or at least part of each I-V converter are integrated on the substrate.

The I-V converters may comprise an operational amplifier and optionally also a dual FET.

The digital signals of the first type received by the means for generating $V_{stim}$ may be converted to corresponding analogue $V_{stim}$ signals by a digital to analogue (D-A) converter provided for each channel.

In a preferred embodiment, the means for generating $V_{stim}$ further comprises a plurality of multiplexers each connected to a D/A converter for receiving the analogue signals of the first type, and a plurality of individually controllable sample and hold circuits, where two or more sample and hold circuits are connected to different outputs from each multiplexer, the means for generating $V_{stim}$ being adapted to provide a real time ramped $V_{stim}$ signal consisting of two or more parts, each part corresponding to a digital signal of the first type, in that the D/A converters are adapted to generate a first analogue signal in response to a first digital signal of the first type and a second analogue signal in response to a second digital signal of the first type, the multiplexer is adapted to provide the first analogue signal on a first output and the second analogue signal on a second output, the individually controllable sample and hold circuits are adapted to receive and hold said first and second analogue signals until controlled to sequentially release the analogue signals so as to form different parts of a ramped $V_{stim}$ signal.

$V_{stim}$ may, for example, be a step function (square pulse) for testing the presence of a giga-seal at a site. Also, $V_{stim}$ may be a series of voltage step functions (square pulses) of increasing amplitude used to rupture cell membrane to provide a whole-cell-measuring configuration.

The main electronic circuit may also be adapted to provide predetermined electric potentials to electrodes of the substrates according to the first, third or fourth aspects for positioning of membranes at the sites.

In a fourth aspect, the present invention provides a high throughput system for determining and/or monitoring electrophysiological properties of ion channels in cells. The system provides high throughput in that most of the processes to be performed are automated and can be performed simultaneously for a large number of cells.

Thus, the system according to the fourth aspect comprises

- a cell incubation unit,
- a compound storage unit,
- one or more substrates according to the first aspect,
- a substrate storage unit,
- a cell positioning and measurement unit for receiving a substrate, said cell positioning and measurement unit comprising means for applying a cell containing liquid to each site of a substrate, means for applying a predetermined potential difference between a predetermined set of electrodes at each site of the substrate in order to position cells at predetermined positions at the sites, and a main electronic circuit according to the third aspect for performing testing and measurements of positioned cells,
- transportation means for transporting substrates from the substrate storage unit to the cell positioning and measurement unit, the transportation means further being adapted to transport cells from the cell incubation unit to the cell positioning and measurement unit, a pipetting system for pipetting compounds from the compound storage unit to a substrate held in the cell positioning and measurement unit, a main computer system for controlling execution of the determination and/or for monitoring and storing the experiment data, said main computer being operationally connected to the one or more electronic processors for data acquisition and analysis, said one or more electronic processors being operationally connected to the digital processing means of the main electronic circuit of the cell positioning and measurement unit, electronic processor means for controlling the transportation means, electronic processor means for controlling the pipetting system.

When writing cell or membrane throughout the present application, any ion transfer channels containing lipid membrane, such as a cell or an artificial membrane can be read.

Electrophysiological properties can be e.g. current flow through an ion channel, electric potential across an ion channel, or capacitance or impedance of an ion channel containing membrane. Moreover, it is possible to add individual test compounds (typically pharmacological drugs) at each membrane holding location, so that individual experiments can be carried out on each membrane. An experiment can be to measure the response of the ion transfer channel to the adding of test compound.

BRIEF DESCRIPTION OF THE DRAWINGS

The present invention is further illustrated by reference to the accompanying drawing, in which.

DETAILED DESCRIPTION OF THE DRAWINGS

The substrate according to the present invention is preferably designed to carry out a large number of individual experiments in a short period of time. This is accomplished by providing a microsystem having a plurality of test confinements each comprising one or more sites for holding membranes, integrated working electrodes connected to data acquisition equipment, means for supplying and positioning ion containing lipid membranes such as cells, and means for supplying carrier, test compound, rinsing liquid, etc. Thereby it is possible to perform independent experiments in each test confinement, and to control the preparation and measurements of all experiments from a central control unit such as a computer. Due to the small size of the test confinements, the invention also permits carrying out measurements utilising only small amounts of test compound. The present invention also provides several different procedures for carrying out measurements.

Figure 1A:
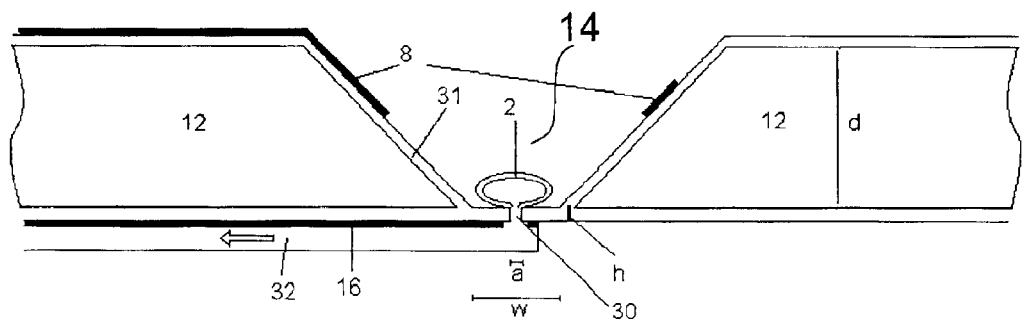
FIGS. 1A and B show a cross-sectional side view and a top view of a substrate having a well with a passage in the bottom part of the well.
Figures 1, 1B:
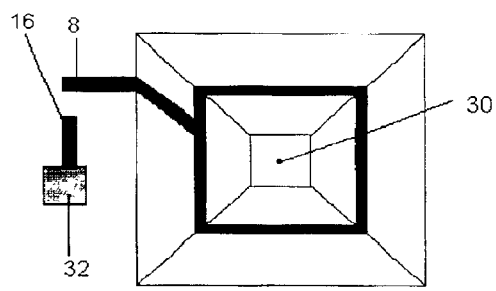

According to the present invention, the substrate can have a number of different configurations. FIG. 1A shows a substrate 12 with a site 14 holding a working electrode 16 and a reference electrode 8. In order to perform electrophysiological measurements on ion channel-containing lipid membranes (hereafter simply denoted as cells) using the substrate 12, the membrane has to establish a barrier separating the working electrode 16 and the reference electrode 8, while still being in electrical contact with both electrodes through an ionic solution. This is obtained by positioning the cell 2 at the passage 30 having a well holding the site 14 and a canal 30 filled with saline. Thereby, by applying an electrical potential difference between the electrodes, the ion channels can support an electrical current between the electrodes through the membrane. The cell 2 should be positioned in a configuration where the working and reference electrodes are electrically separated so that current can only be conducted through the membrane, the cell should form a high resistance seal, a giga-seal, with the substrate. Preferably there is piping 32 for applying suction to the passage on the bottom side of the substrate. The piping 32 leads to the upper side of the substrate, and may include the electrical wiring to the working electrode 16 as shown in FIG. 1B.

In FIG. 1A, a site 14 is a region in electrical contact with the reference electrode 8 and the working electrode 30 and adapted to hold a cell in that the surface material is well suited for creating a seal with the membrane. Such materials include silicon, plastics, pure silica and other glasses such as quarts and Pyrex or silica doped with one or more dopants selected from the group of Be, Mg, Ca, B, Al, Ga, Ge, N, P, As and oxides from any of these. Correspondingly, the substrate itself can consist of any of these materials.

It is an important aspect that the substrate 12 can provide some means for separating sites where different compounds are to be tested. A volume for holding an amount of liquid for performing measurements with a given compound or a reference measurement will be denoted a test confinement. Test confinements preferably hold small volumes in order to minimise the necessary amounts of the often expensive test compounds, moreover, the time needed for mixing of the produced solutions by diffusion, decreases with decreasing volume. A test confinement can contain one or more sites. In the embodiment of FIGS. 1A and B, a site is a geometrically shaped structure on the substrate. The function of the shaping is both to aid the positioning of a cell 2 within the site and to separate test confinements, which in this case consists of single sites. Alternatively, the well may have two or more sites arranged at the bottom part of the well.

In the following, two preferred embodiments of substrates according to the invention are described in relation to FIGS. 2A–C and 3A–C. The Figures are not to scale.

The substrates of FIGS. 2A–C and 3A–C are basically a substrate holding a plurality of truncated pyramids, possibly having cavities with one or more passages 30 at the apex. The base of the pyramid is a square. The top angle of the pyramid is 2×54.7 o, the wafer thickness d=280–650 $\mu$m, the side-length at the apex of the pyramid is w≈30–60 $\mu$m in order to allow room for a cell. The apex of the pyramid is covered with a Silicon-dioxide or silicon-nitride membrane 31 of thickness h≈0.1–3 $\mu$m. In this membrane a passage of diameter a≈0.5–5 $\mu$m is formed. The pyramid may be oriented as in FIGS. 2A–C where the pyramid is formed on the lower side of the substrate with the apex upwards or as in FIGS. 3A–C on the upper side of the substrate with the apex downwards. The functions in the two orientations are different, in the embodiment of FIGS. 2A–C, the pyramid contributes to the pump path in the first canal, whereas in the embodiment of FIGS. 3A–C, the pyramid contributes to the positioning of cells.

The devices can be fabricated in several quite different ways. Below, three different fabrication processes for the basic structure are summarised. First the method oxide first used for fabricating the above mentioned design, second an alternative oxide last process, and third another alternative deposited glass process.

Oxide First Process
Grow 1–3 $\mu$m wet thermal $SiO_2$ covering whole substrate.
Define the passage on the bottom side of the substrate by photomasking and Reactive Ion Etching to make the passage through the oxide to the silicon substrate.
Deposit LPCVD Silicon-nitride for an etch mask on both sides of the substrate.
Define nitride windows to form pyramid base plane on the upper side of the substrate by photomasking and Reactive Ion Etching and wet oxide etching (buffered Fluoric Acid)
Etch pyramidal cavities through the windows by anisotropic etching in the silicon. This creates pyramid sides with a slope of 54,7°.
Strip nitride etch stop using Hot $H_3PO_4$.
Grow 0.1–1 $\mu$m wet thermal $SiO_2$ to electrically isolate the bulk Silicon wafer in order to cover the sides of the pyramid. Other $SiO_2$ regions will not grow considerably.

Oxide Last Process
Form an etch-stop layer in silicon (Boron doping) on the bottom side of the substrate, using either doping by implantation or epitaxial growth. The etch stop layer will typically be around 1 $\mu$m thick.
Deposit LPCVD Silicon-nitride for an etch mask on both sides of the substrate.
Define nitride windows to form pyramid base plane on the upper side of the substrate by photomasking and Reactive Ion Etching and wet oxide etching (buffered Fluoric Acid).
Etch pyramidal cavities through the windows by anisotropic etching in the silicon. This creates pyramid sides with a slope of 54,7°. The etching stops on the Boron doped etch stop to form an ~1 $\mu$m thick silicon membrane.
Strip nitride etch stop using Hot $H_3PO_4$.
Define the passage on the bottom side by photomasking and Reactive Ion Etching of Silicon.
Grow wet thermal $SiO_2$ to convert the Silicon membrane into an oxide everywhere on the substrate. This process narrows the passage since $SiO_2$ is also formed inside the passage, which thereby can be made smaller compared to what is possible using photolithography.

Deposited Glass Process
Deposit 200–500 Å Silicon-dioxide on both sides of a silicon substrate using a wet thermal deposition process.
Deposit 1000–5000 Å Silicon-nitride on both sides of the substrate using an LPCVD process.
Define nitride windows to form pyramid base plane on the upper side of the substrate, and define the passage on the bottom side, by photomasking and Reactive Ion Etching and wet oxide etching (buffered Fluoric Acid).
Etch pyramidal cavities through the windows by anisotropic etching in the silicon. This creates pyramid sides with a slope of 54,7°. The Silicon-nitride protects the substrate against the etching agent.
Deposit 100 nm–3 $\mu$m silicon-oxide or other glass types on the silicon-nitride membrane. The glass can be deposited using sputtering, PECVD, or LPCVD-processes, followed by thermal annealing.

For all three fabrication processes the main concern during processing is the mechanical stability of the $SiO_2$ membrane with the passage during the final high temperature oxidation step. The surface material on the two first embodiments (here $SiO_2$) can optionally be coated with Silicon-nitride, in order to prevent a contribution to the electrical conductivity.

Working and reference electrodes can now be formed. The working electrode on the bottom side can be formed using standard deposition and photolithography techniques. The reference electrode is preferably formed using evaporation of conducting material through a shadow mask. As shown in FIGS. 1B, and 3B, the reference electrode 8 can be shaped so as to at least partly encircle the site in the bottom of the well. Alternatively the electrodes are located on other substrates to be applied on the top and bottom of the substrate.

Further, canals for liquid handling and cell positioning may possibly be created in the substrate, the flow canal having an inlet/outlet elsewhere on the substrate. Alternatively, the canals are fabricated on other substrates to be applied on the top and bottom of the substrate. As will be described in detail later, the canals are designed to facilitate generation of electroosmotic flow.

The described features are preferably arranged such that there is an easy access to all connection in- and outlets from above the assembly, as illustrated in FIG. 1B (suction outlet 32, contacts to working electrode 16 and reference electrode 8). This configuration is adapted for applying a unit, having similar but reverse in- and outlets, on top of the assembly.

Figure 2A:
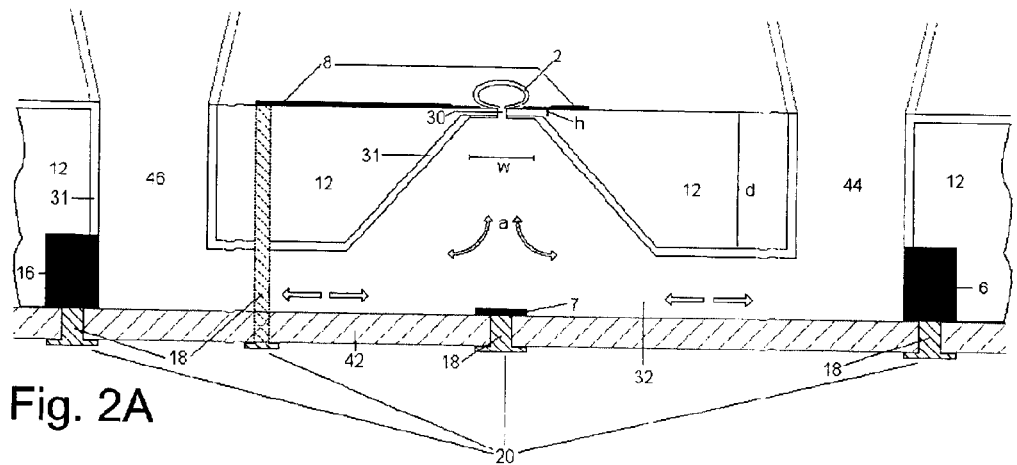
FIGS. 2A–C and 3A–C show a cross-sectional side view, a top view and a bottom view of two different embodiments of substrates having a passage connected to a canal in the substrate.

In a preferred embodiment shown in FIG. 2A, the substrate comprises a plurality of wells similar to the wells of the substrate described in relation to FIG. 1. In addition, the substrate comprises a canal 32 with two openings 44 and 46 in connection with each well. Canal openings 44 and 46 are on the upper wet side of the substrate as illustrated in the top view of FIG. 2B. The working electrode 16 is positioned near the passage 30 in the canal 32. The canal 32 also has two extra electrodes 6 positioned towards the canal openings 44 and 46. Electrodes 16 and 6 are adapted to provide an electrical potential and/or a current in a liquid filled canal 32 in order to generate an electroosmotic flow as will be described in detail later. The flow in the canal can be used to create a flow through the passage 30. Hence, in this embodiment, the working electrode 16 has two functions, measurement and flow generation, which may be provided by two individual electrodes. The horizontal shape of the canal is illustrated on FIG. 2C, which shows a bottom view with plate 42 removed.

Figure 2B:
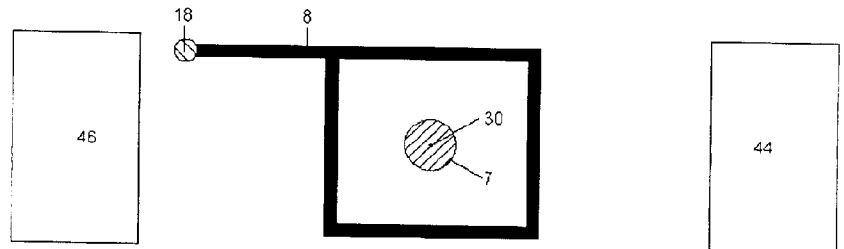
Figure 2C:
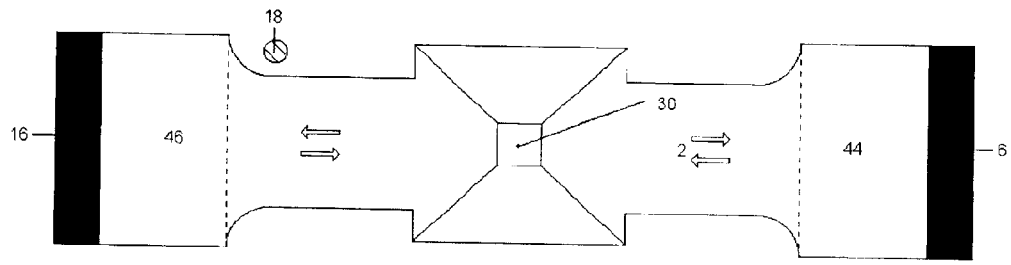
Figure 3A:
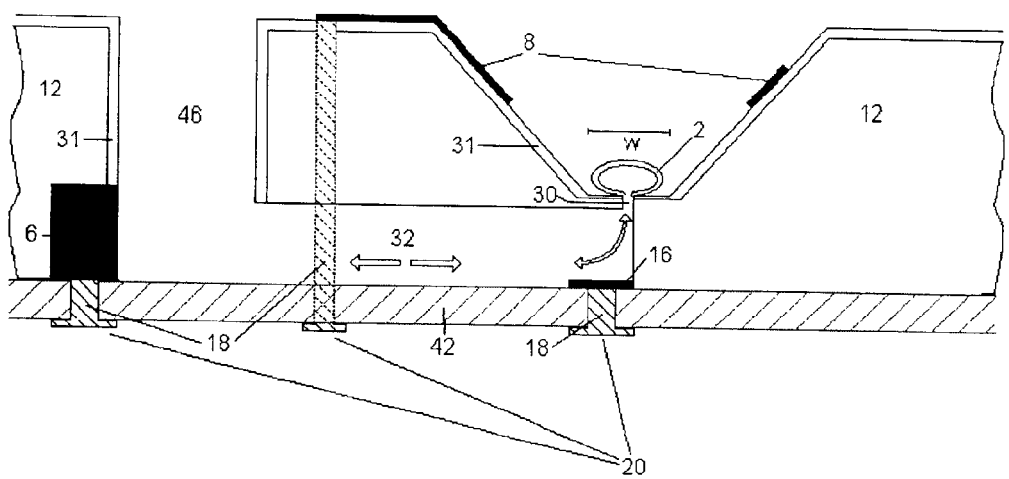
Figure 3B:
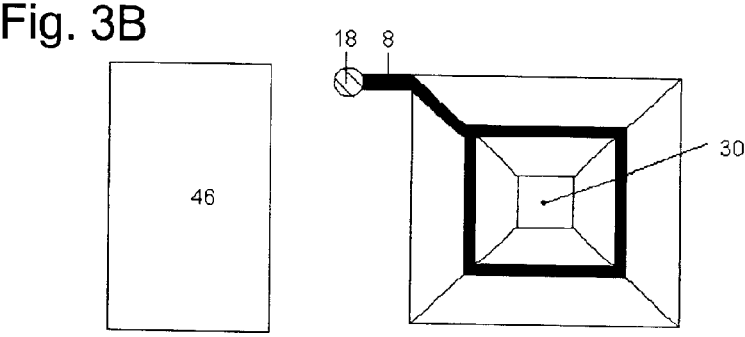
Figure 3C:
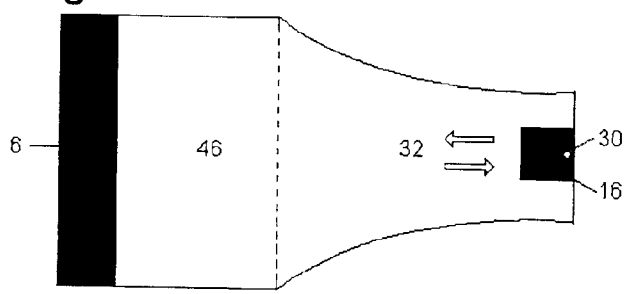

Another embodiment similar to the embodiment described in relation to FIGS. 2A–C is shown in FIGS. 3A–C. As can be seen on FIG. 3A, the canal has only one opening 46 at the upper surface of the substrate since the other opening of the canal is formed by the passage 30. In this embodiment, the flow can still be induced so as to generate a flow in the passage out from or into the canal simply by applying a potential difference between the working electrode 16 and the electrode 6. FIGS. 3B and 3C show a top view and bottom view respectively.

In the embodiments of FIGS. 2A–C and 3A–C, electrodes 6, 16 and 8 have lead-in electrodes 18 through the substrate 12 and bottom plate 42 to contact pins 20 in order to provide all electrical connections on the dry backside of the substrate.

The canal 32 can be formed as a canal on the backside of substrate 12 and later covered by the plate 42. The canal can be formed by depositing a thick (about 30 $\mu$m) film of SiO2 followed by definition and formation of the canal using photolithography and etching. Alternatively the canal can be formed by depositing SU-8 photoepoxy, using photolithography.

Obtaining good contact between the cell and a glass pipette, and thereby creating a giga-seal between a cell and the tip the pipette, is well described in the prior art. In the case of the substrates according to the present invention, suction can not always be provided, and the positioning of the cells is carried out by other means. It has been shown that the mere contact between the cell membrane and the substrate, typically ultra-pure silica, is sufficient for the cell to make some bonding to the surface and create a giga-seal.

Figure 9A:
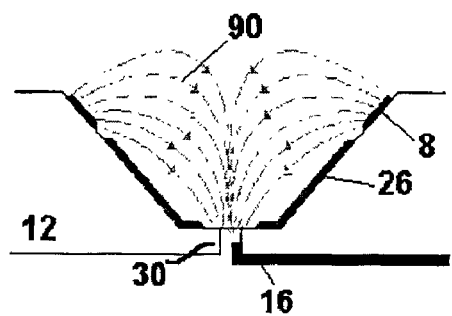
FIGS. 9A & 9B shows cross sectional and top views of an electrode configuration with electrical radial converging field lines.

The substrate technology raises several problems regarding the positioning of cells on a substrate. Several cells are applied to one chamber where one cell has to be positioned at an exact position and it has to stick to that location. The remaining cells are considered as waste and may be removed. For the purpose of cell positioning, the sites may be coated with a film made of a hydrophobic material in regions where cells should not attach and with a hydrophilic film where the cells should attach. As shown in FIGS. 9A and B, a hydrophobic material 26 may cover the surface of the substrate within a test confinement except at regions just around electrodes. Thereby, cells can only bind themselves at the sites.

Providing the hydrophobic/hydrophilic regions can be done by micropatterning specific locations so as to define a patterned adhesiveness on the substrate. E.g. hydrophobic silane or Teflon, or other types of polymer can define regions where membranes should have low adhesiveness whereas hydrophilic silicon dioxide or multiple layers of silicon nitride and silicon dioxide can define regions where membranes should have high adhesiveness. It has been shown that cell attachment factors such as e.g. poly-L-lysine, vitronection or fibronectin do not bind to the hydrophobic regions. Treatment of the micropatterned material with one of such factors will give cell adhesiveness in all regions but the hydrophobic.

Figure 10A:
FIGS. 10A to G show different procedural step for fabricating a region of hydrophobic/hydrophilic material such as the hydrophilic region shown in FIG. 8.
Figure 10B:
Figure 10C:
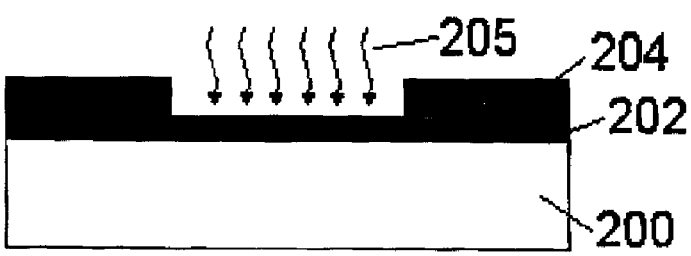
Figure 10D:
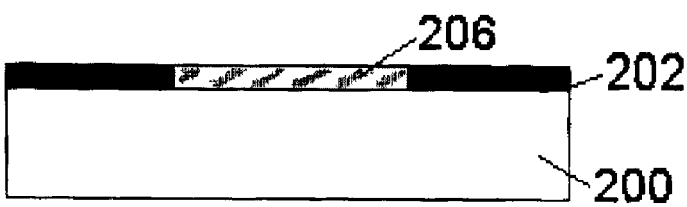
Figure 10E:
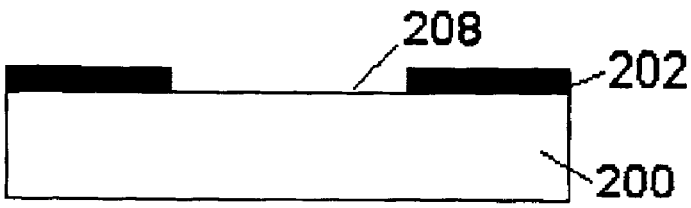
Figure 10F:
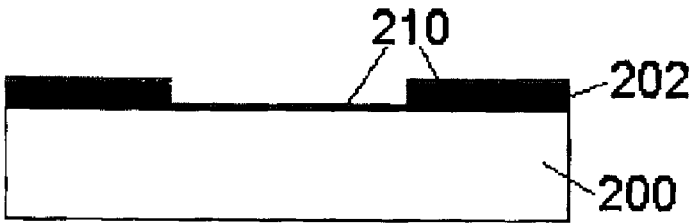
Figure 10G:
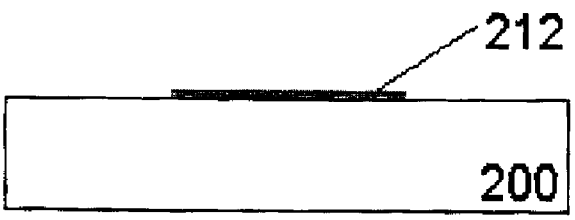

The micropatterning of both hydrophobic and hydrophilic material can be fabricated using standard photolithography methods as outlined in FIGS. 10A to G for a hydrophobic region. FIG. 10A shows the clean silica substrate 200, which is spin coated with a photo resist 202 as shown in FIG. 10B. Using a mask 204 and light exposure 205 as shown in FIG. 10C, followed by development of the exposed resist 206 of FIG. 10D, a "resist free" region 208 is defined on the substrate 200 as shown in FIG. 10E. The pattern of the final layer corresponds to the "resist free" region 208 and is defined by the mask 204. Now, a layer of hydrophobic material 210 can be deposited on the substrate, FIG. 10F. The material may be deposited using e.g. standard CVD techniques or by simply exposing the substrate to a hydrophobic material such as silane or Teflon. In FIG. 10G, the photo resist is removed by etching, leaving a region 212 of hydrophobic material having a desired shape.

In order to define a hydrophilic pattern, a hydrophilic material may be deposited instead of hydrophobic material 210 in FIG. 10F. As will be known to the person skilled in wafer processing technology, a wide variety of different procedural steps may be used in the fabrication, giving rise to similar patterned regions.

The positioning of cells at a site can be carried out using electric fields. In electrophoresis, electrically charged particles are moved in a fluid under the influence of an electric field. If it is the liquid rather than the particles which is set in motion, e.g. by creating a flow of an ionic liquid in a canal, the phenomenon is called electroosmosis. When electric fields are used to guide cells in microscopic structures a number of parameters must be considered which typically do not play a role in macroscopic structures.

In the substrate embodiments described in relation to FIGS. 2A–C and 3A–C, the positioning of a cell, vesicle or liposome can be carried using electroosmosis to generate an electroosmotic flow (EOF) in the canal 32. When using electroosmosis, a liquid flow is generated in a canal by applying an electric field across the liquid using electrodes 6 and 16. The flow will generate a flow in vessels communicating with the canal such as from the well through the aperture 30. In the following, some important considerations related to electroosmosis are described in relation to FIG. 4A and some specific embodiments of electroosmotic flow pumps (EOPs) are presented in FIGS. 5 through 8.

Figure 4A:
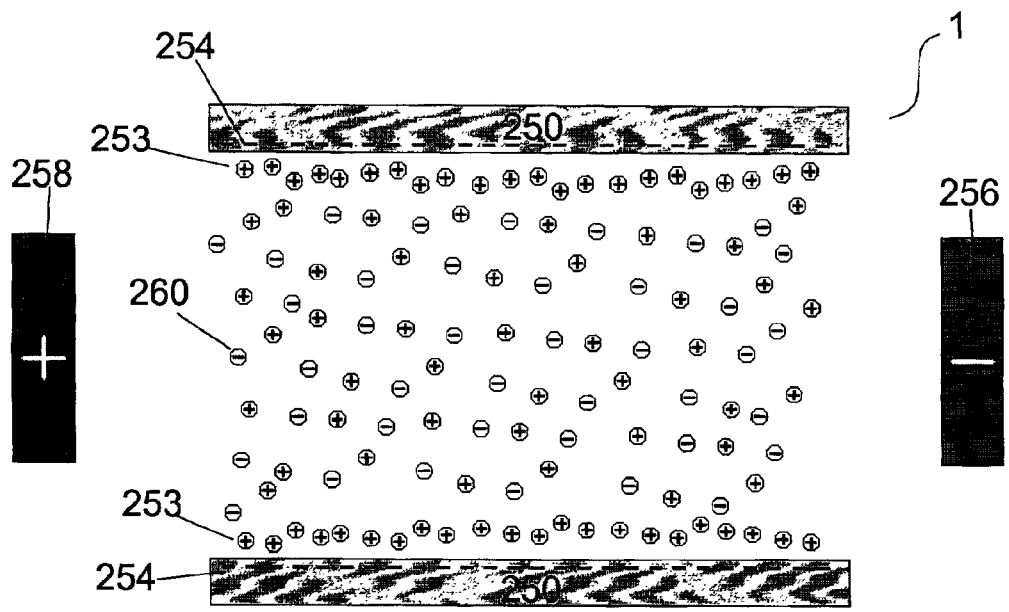
FIG. 4A illustrates details of electroosmotic liquid flow through a canal and 4B is a graph showing the flow conductance versus hole diameter for the passage between the upper and lower part of the substrate. This exemplifies the needed performance of electroosmotic pumps used in embodiments of the present invention.

Electroosmotic flow is generated by application of an electric field through a solution in a canal defined by insulating walls, a schematic illustration of a canal 1 is shown in FIG. 4A. The canal is formed by walls 250 with electrodes 256 and 258 in each end. A liquid held in the canal is an ionic solution having positive ions 253 and negative ions 260.

The phenomenon depends on ionisation of electronegative sites 254 on surfaces of the walls 250 so that for electroneutrality there is an excess mobile charge in the solution, predominantly located close to the walls within a thin screening layer given by the Debye length $\lambda_D \approx 1$–10 nm for the interface. An electric field applied to the solution acts on the excess charge screening layers causing the fluid to flow. The quantity and distribution of excess charge in the solution depends on the surface material (density of ionisable sites) and on the solution composition, especially pH and ionic concentration. The charge distribution is related to a parameter, the zeta ($\zeta$) potential, which determines the strength of the electroosmotic flow. However, although values for the zeta potential are measured and published for material/solution combinations it is not really a readily controllable parameter, and as it arises from the ionisation of surface sites, $\zeta$ and EOF are very susceptible to changes in surface condition and contamination. A value of 75 mV for $\zeta$ is given in the literature for a silica surface. For glass the values may be twice those for silica but for both the effects of pH and adsorbing species can in practice very significantly reduce the values. Such a value for $\zeta$ may be used in design calculations but it is wise to ensure that adequate performance is not dependent on it being achieved in practice. The direction of EOF is determined by the excess mobile charge in the solution generated by ionisation of the surface sites. As pKa for the ionisable groups on silica or silicate glass is ~2, then at neutral pH values the surface is negatively charged and EOF follows the mobile positive ions towards a negatively polarised electrode. The volume flow rate $I_{vol}^{eof}$ associated with electroosmotic flow for a flow canal of length L, and constant cross sectional area A is given by $$I_{vol}^{eof} = \frac{A\varepsilon\zeta}{L\eta}U, \quad (1)$$

where $\varepsilon$ is the permittivity and $\eta$ the viscosity of the liquid, while $\zeta$ is the zeta potential of the interface between the liquid and the canal boundaries. U is the driving voltage applied across the ends of the canal with length L and constant cross sectional area A. Eq.1 defines the maximum possible flow rate an EOF pump can deliver with no load connected. The average velocity of the fluid particles in the canal is in general given by $u = I_{vol}/A$, and the electricfield strength by $E = U/L$, allowing the definition of the electroosmotic mobility $\mu_{eof} = u/E = \varepsilon\zeta/\eta$ to be independent of any particular geometry of the flow canal containing the EOF pump, and solely to characterise the interface between the liquid and the walls. With a load connected to the pump, the EOF driving force will be accompanied with a pressure driven flow (Poiseuille flow). The volume flow rate associated with laminar Poiseuille flow is given by $I_{vol}^{Poiseuille} = K_{channel}\Delta p$, where $\Delta p$ is the pressure difference across each end of the flow canal, and $K_{canal}$ the flow conductance of the canal. The total flow rate is then given by $$I_{vol} = K_{channel}\Delta P + \frac{A\mu_{eof}U}{L}. \quad (2)$$

The pressure compliance of the pump is found by putting $I_{vol}=0$, and solving for $\Delta p$:

$$\Delta p_{max} = \frac{I_{vol}^{eof}}{K_{channel}}. \quad (3)$$

The overall performance of any particular EOF pump can be quantified by the performance power given by the product $\Delta p_{max} I_{vol}^{eof}$, which is a quantity expressed in the unit Watt. The higher power, the better is the overall performance of the pump. If the pump is loaded with flow conductance $K_{load}$ at one end, and a reference pressure at the other end, the pressure difference across the load relatively to the reference pressure is given by:

$$\Delta p_{load} = \frac{-I_{max}}{K_{load} + K_{channel}}, \quad (4)$$

while the volume flow through the load is given by $$I_{vol}^{load} = K_{load}\Delta p_{load}. \quad (5)$$

A specific choice of pump configuration will give rise to an electrical conductance of the pump canal $G_{canal}$. In response to the EOF driving voltage, the electrolyte inside the pump canal will carry the electrical current $I_q$. Design considerations associated with EOF pumps should comprise heat sinking due to the power dissipation in the pumps. Moreover, the location and design of electrodes should be considered. In an electrophysiological device, the natural choice of electrode material is AgCl, and hence the consumption of such electrodes when operating the pump should be considered. The rate of consumption of electrode material expressed in volume per time unit is given by:

$$\Delta V_{\Delta t} = \frac{I_q m_{AgCl}}{eN_A\rho_{AgCl}}, \quad (6)$$

where $m_{AgCl}=143.321$ g/mol and $\rho_{AgCl}=5.589$ g/cm$^3$ is the molar mass and the mass density of AgCl, while $e=1.602\times 10^{-19}$ C and $N_A=6.02\times 10^{23}$ mol$^{-1}$ is the elementary unit of charge and the Avogadro constant.

An alternative to the use of consumable electrodes is suggested which involves providing an external electrode linked to the chamber by an electrolyte bridge with high resistance to hydrodynamic flow. This might be a thin canal, similar to that providing the EOF pumping, but with a surface having low density of charged sites (low zeta potential) or where the surface has opposite polarity charge to the EOF pumping canal. In the latter case the low flow conductance canal to the counter electrode contributes towards the EOF pumping. Most wall materials tend, like glass or silica, to be negatively charged in contact with solutions at neutral pH. However it is possible to identify materials which bear positive charge. Aluminium based ceramics may be suitable, especially if solutions are on the low pH side of neutral. Alternatively polymer or gel material, such as Agarose, polyacrylamide, Nafion, cellulose acetate, or other dialysis membrane-type materials may produce the bridge with high resistance to hydrodynamic flow. Preferably these should have low surface charge density or an opposite polarity to that of the EOF pumping canal.

In the following three possible realisations of EOF pump geometries will be described, and their performance compared.

Figure 5A:
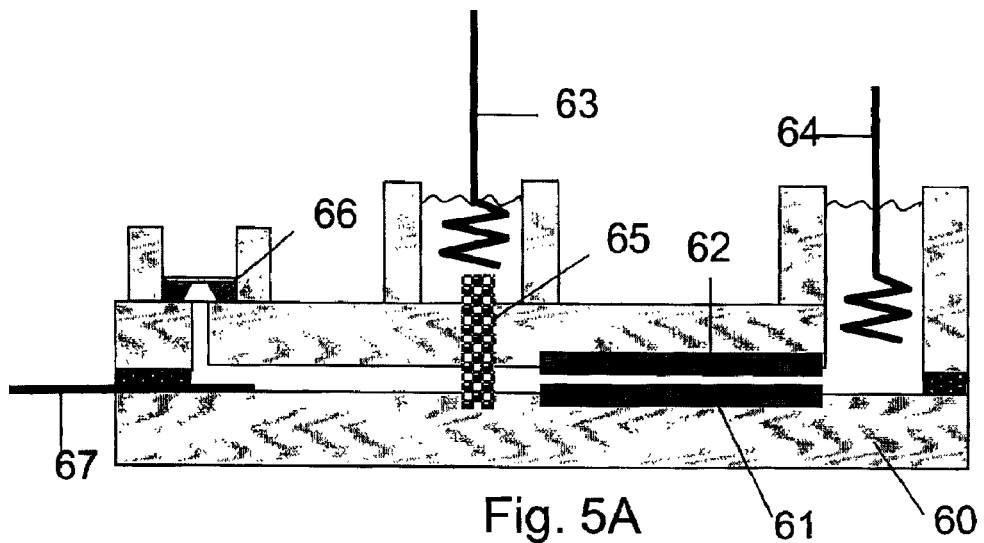
FIGS. 5A and B, 6A and B, and 7A and B are cross sectional and top views of electroosmotic flow pumps used in embodiments of the present invention.

In a parallel plate EOF pump, shown in FIGS. 5A and B, thin spacers inserted between two plates with silica or glass surfaces define the pump canal. The pump canal has width W, length L, and height (i.e. distance between the plates) h. The electrical conductivity of the solution is $\sigma$ (approximately 0.014 S cm$^{-1}$ for a 150 mM aqueous solution of sodium chloride). A possible realisation of the pump configuration is shown in FIGS. 5A and B. The width of the canal should be much greater than the height and the length. Such pump geometries are readily realised by glass plates mounted in a laminated polymer holder with the spacing maintained by polymer spacer balls or spacers shaped by photolithography in SU-8 resist. Below are listed the key pump parameters. Other parameters may easily be computed from Equations 1–5.

| Canal flow conductance | Max flow | Electrical conductance |
|---|---|---|
| $K_{channel} = \dfrac{Wh^3}{12\eta L}$ | $I_{max} = \dfrac{Wh}{L}\mu_{eof}U$ | $G_{channel} = \dfrac{Wh}{L}\sigma$ |

Figure 6A:
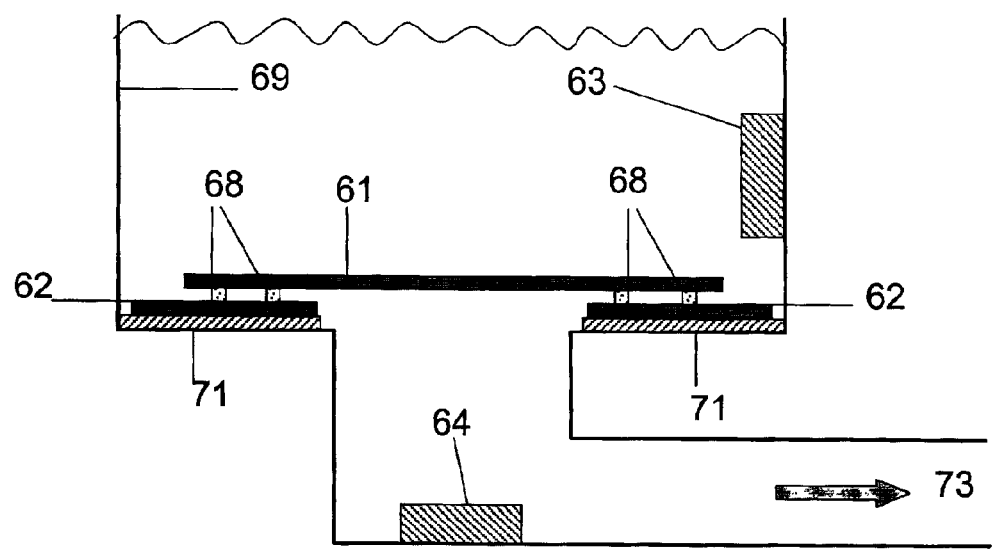

A Corbino disc EOF pump is shown in FIGS. 6A and B is, as the parallel plate configuration, also based on plates with silica or glass surfaces separated by spacers. However, in this geometry the plates have annular shape and the flow is radial with a drain in the centre. The distance h between the plates again has to be small compared with both the inner ($r_{in}$) and outer ($r_{out}$) radius of the annulus. This pump configuration is particularly suitable for integration into a pipetting well. The key parameters are given below

| Canal flow conductance | Max flow | Electrical conductance |
|---|---|---|
| $K_{channel} = \dfrac{\pi h^3}{6\eta \ln\left(\frac{r_{out}}{r_{in}}\right)}$ | $I_{max} = \dfrac{2\pi h}{\ln\left(\frac{r_{out}}{r_{in}}\right)}\mu_{eof}U$ | $G_{channel} = \dfrac{2\pi h}{\ln\left(\frac{r_{out}}{r_{in}}\right)}\sigma$ |

Figure 7A:
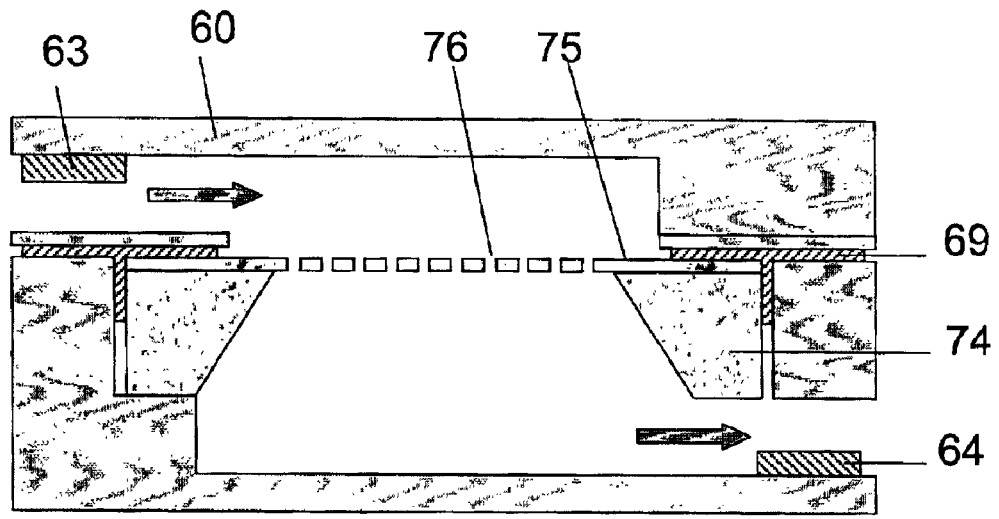

A sieve EOF pump is fundamentally different from the two previous examples. Here the flow canal of the pump is defined as a number N of small holes in silica or glass membrane. Similar effects may be achieved by flow through a porous material forming a $\zeta$ potential with the liquid. This pump may be manufactured using the same microfabrication process as for the passage used for sealing to the cell. Instead of only one hole, an array of holes should be made in the membrane. The key parameters for this configuration are however not as analytically easy to compute as the previous examples, and one has to rely on an experimentally determined flow conductance for a single passage $K_{passage}$, and a geometrical factor $F_{geometry}$ accounting for the effective canal length, which in the case for the hole diameter d being comparable with the membrane thickness $t_m$, should be asserted somewhat longer than the actual membrane thickness. FIGS. 7A and B shows the principle of this pump configuration. The sieve configuration is in particular feasible if a spatially very small and compact pump is needed. The drawback of this configuration is the difficulty of heat sinking, inherent to this geometry. Below are listed the key parameters.

| Canal flow conductance | Max flow | Electrical conductance |
|---|---|---|
| $K_{channel} = NK_{orifice}$ | $I_{max} = \dfrac{N\pi\left(\frac{d}{2}\right)^2}{t_m F_{geometry}}\mu_{eof}U$ | $G_{channel} = \dfrac{N\pi\left(\frac{d}{2}\right)^2}{t_m}\sigma$ |

Below are given the key parameters for actual choices of pump dimensions. Feasible pump dimensions for applications related to microfluidics in an electrophysiological device would be:

Parallel plate pump W=0.5 cm, L=0.5 cm, h=0.5 $\mu$m.
Corbino disc pump $r_{out}$=0.25 cm, $r_{int}$=0.1 cm, h=0.5 $\mu$m.
Sieve pump $t_m$=1 $\mu$m, d=1 $\mu$m, N=10, $F_{geometry}$=2.

Figure 4B:
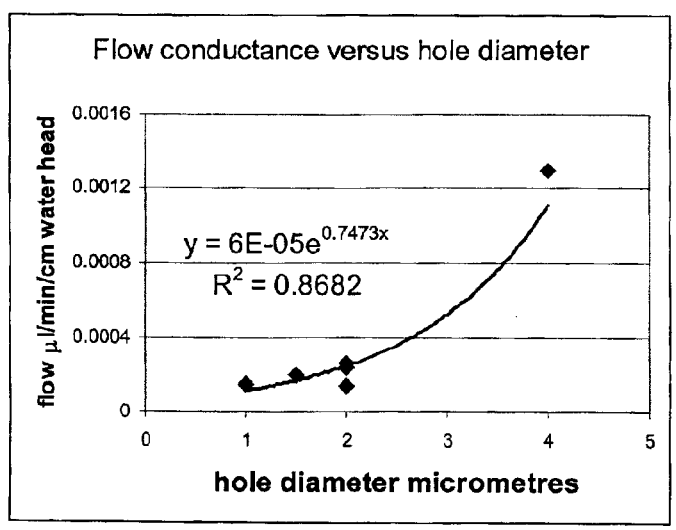

The calculations are based on conditions relevant for an electrophysiological device, where the liquid used is a physiological buffer solution. However, for most purposes the data corresponding to 150 mM NaCl solution are representative. The asserted electrical conductivity is $\sigma$=0.014 S cm$^{-1}$ and the viscosity $\eta$=8.94×10$^{-4}$ kg m$^{-1}$s$^{-1}$. The calculations are based on a voltage drive of U=100 V, and a conservative choice for the zeta potential $\zeta$=15 mV. The flow conductance of the cell receptor passage, which is assumed to be the most significant load to the EOF pump, was determined experimentally for a number of hole diameters and is shown in FIG. 4B.

In the calculations a flow conductance $K_{passage}$=3 pl s$^{-1}$ mbar$^{-1}$ corresponding approximately to a 1 $\mu$m diameter hole is assumed.

| Parameter | Parallel plates | Corbino disc | Sieve |
|---|---|---|---|
| Flow conductance of pump canal $K_{canal}$ [pl s$^{-1}$ mbar$^{-1}$] | 1.17 | 7.99 | 30.0 |
| Maximum volume flow rate $I_{max}$ [nl s$^{-1}$] | 0.58 | 4.00 | 4.58 |
| Maximum pressure $\Delta p_{max}$ [mbar] | 500.7 | 500.7 | 152.7 |
| Performance power $\Delta p_{max} I_{max}$ [nW] | 29.2 | 200 | 70.0 |
| Pressure difference across load $\Delta p_{passage}$ [mbar] | 140.1 | 364.0 | 138.9 |
| Volume flow rate in load $I_{passage}$ [nl s$^{-1}$] | 0.42 | 1.09 | 0.42 |
| Electrical conductance of pump canal $G_{canal}$ [$\mu$S] | 0.70 | 4.80 | 11.0 |
| Electrical current through pump canal $I_q$ [$\mu$A] | 70.0 | 480 | 1100 |
| Power dissipation in pump U $I_q$ [mW] | 7.0 | 48 | 110 |
| Maximum thermal resistance of required heat sink to keep temperature rise below 20 C° [C°W$^{-1}$] | 2857 | 416.7 | 181.9 |
| Rate of consumption of AgCl electrodes $\Delta V_{At}$ [$\mu$m$^3$ s$^{-1}$] | 18610 | 127800 | 292400 |

Priming is understood as the process, required to fill the device under consideration by liquid for the first time before operation. The electroosmotic driving force requires, that both electrodes are immersed in liquid before flow can be achieved. The different EOF pump configurations proposed may to some extent prime spontaneously by means of capillary forces in the narrow flow canals. However, it may not be possible to prime the whole pump chamber containing both electrodes solely by means of capillary forces. Considering the rate of consumption of the AgCl electrodes, thin film electrodes deposited between the glass plates are not likely to endure the whole operational cycle of the device. For the sieve configuration the situation may be even worse. Despite the device under consideration is considered to be disposable, bulk electrodes are preferable. A feasible solution to this problem could be the use of adequately located thin film electrodes only for priming of the pump chamber containing the bulk electrodes. The bulk electrodes can take over after the priming procedure. Another possible solution would be to prime the whole device by means of gas pressure drive applied to the pump and pipetting ports before proper operation. Even for devices with many parallel measure sites, the priming could readily be done for all sites in parallel, by pipetting liquid onto all sites and priming by gas pressure applied to all sites simultaneously.

In one possible cell positioning procedure, flow canals on both the front side and the rear side of the passage are incorporated into the device. The front side refers to the side where cells are loaded, and the extra cellular reference electrode for the electrophysiological measurement is placed, while the rear side refers to the side where suction is applied to drag the cells onto the passage, and where the intracellular electrode is placed. The front side flow canal passes over the passage, and is connected to a pump (EOF pump or any other pump with similar performance) at one end, and a pipetting well at the other end. The volume of the front side flow canal should be adequately low to ensure that once a cell has entered the canal, a flow maintained by the rear side pump to the passage is capable, within a short time, of dragging the cell to the position of the passage to establish the giga seal. A narrow front side flow canal enables the detection of cells passing the canal using the same principle as in a Coulter counter. The detection may be realised by an electrical measurement of the canal electrical resistance with two electrodes, one at each end of the canal. When a cell enters the flow canal it expels a volume of buffer solution, which consequently cannot contribute to the conductance. The relative change in electrical resistance is therefore given by the ratio of cell volume to canal volume. In addition a spreading resistance contribution is expected. This is however small if the cross sectional area of the cell is small compared to the cross sectional area of the flow canal. The change in canal resistance is calculated by:

$$\Delta R = R_c \frac{V_{cell}}{V_c} F_s, \qquad (7)$$

where $V_{cell}$ and $V_c$ are the volumes of the cell and the canal respectively. $R_c$ is the electrical resistance of the canal and $F_s$ is the geometrical factor accounting for the spreading resistance associated with a cell being inside the canal. $F_s$ is a number slightly larger than 1, and depends on the relative cross sectional areas of the cell and the flow canal. If canal width becomes comparable to cell size, the geometrical factor may however be quite large, corresponding to the situation where the spreading resistance dominates over the buffer volume exchange effect. The rear side flow canal need not be very narrow, and should be equipped with either one pump port at one end and connected directly to the passage at the other end, or alternatively equipped with two pump ports, one at each end with the passage placed in the middle of the canal. The two pump ports version should be chosen if exchange of the intracellular buffer is desired during operation of the device. A statistical approach may be employed in order to estimate the required waiting time before a cell loaded into the pipetting well connected to the front side flow canal has passed the canal with a certain probability. This probability will mainly depend on the concentration of cells in the suspension $C_c$, the average flow velocity $U_c$ in the front side flow canal and the cross sectional area $A_f$ of the flow canal. The average number of cells passing the canal during the time t can be found from:

$$\beta(t) = C_c A_f u_c t. \qquad (8)$$

The probability p(t) that at least one cell has passed the canal during the time t is then given by the Poisson distribution:

$$p(t) = \sum_{n=1}^{\infty} \frac{\beta(t)^n \exp(-\beta(t))}{n!} \qquad (9)$$

To demonstrate this positioning scheme one may for simplicity of calculation assume a front side flow canal of circular cross section of radius $r_c = 25$ $\mu$m and length $L_c = 0.25$ mm. The volume and flow conductance of this flow canal is respectively given by $V_c = 0.5$ nl and $$R_c - \frac{}{8\eta L} = 69 nls^{-1} mbar^{-1}.$$

The average flow velocity of pressure driven Poiseuille flow will be 35 mm s$^{-1}$ per mbar of driving pressure difference. For a typical cell radius $r_{cell} = 6$ $\mu$m, the resistance change given by Eq.7 will be approximately 177Ω out of the total canal resistance of 90.9 kΩ, i.e. a relative change of 0.19%. Here a geometrical factor of 1.06, accounting for the spreading resistance, has been assumed. With a front side drive pressure difference of only 1 mbar, within 2 seconds 4.1 cells will on average have passed the canal, and at least one cell will have passed with probability 98.4%. This positioning scheme relies on the ability to stop the front side flow as soon as a cell has entered the canal. This requires fast electronics, and a method to avoid this is to consecutively apply small pressure pulses to the front side flow canal, until the presence of a cell inside the canal is detected by means of the Coulter counter principle. Considering the tiny volume of the front side flow canal any of the proposed EOF pump types mounted on the rear side flow canal would be able to suck the cell into position at the passage within a fraction of a second. The cell detection electronics of the Coulter counter can be made of the same type as needed in the electrophysiological measurements of ion channel response.

Figure 5B:
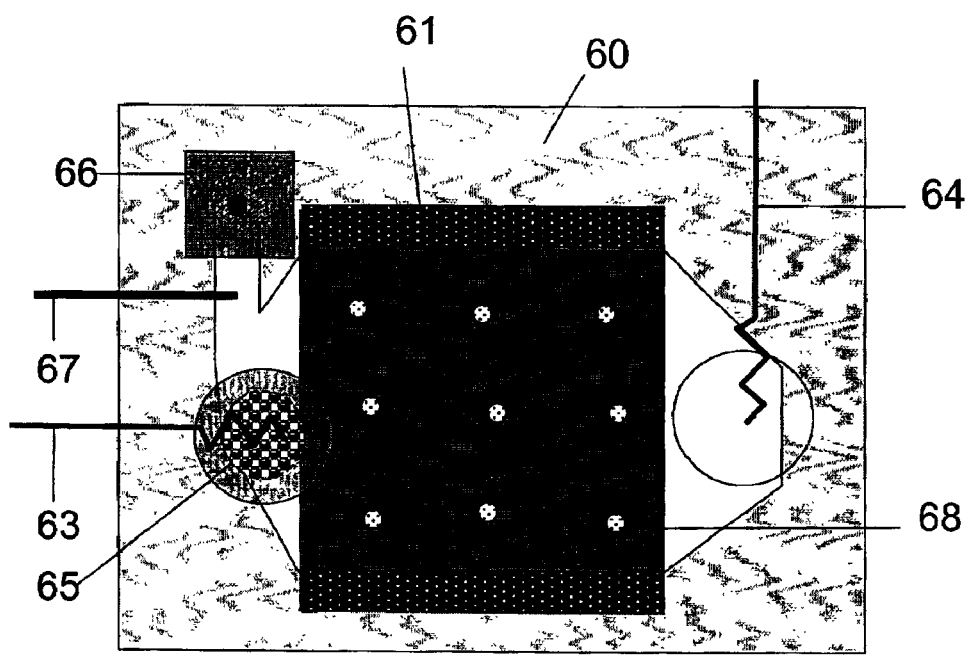

FIGS. 5A and B show an embodiment of a parallel plate EOF pump integrated with the cell measurement site. FIG. 5A shows a side view of the device while FIG. 5B shows a top view. This drawing only considers the rear side liquid handling system, containing the intracellular buffer solution. A housing 60 contains two parallel plates 61 and 62 with glass or silica surfaces. When an electrical ion current is drawn between the electrodes 63 and 64, the pumping action takes place in the liquid-filled space between these surfaces. A region with gel material 65 comprises an electrical current bridge with high hydrodynamic flow resistance around electrode 63. The EOF pump composed of these sub-units controls the flow through the passage of the cell measurement site 66. An additional measurement electrode 67 is added to supply a low impedance current path to the measurement site. Spacer blocks 68 are inserted between the parallel plates 61 and 62 in order to ensure the sub-micrometer distance between them.

FIGS. 6A and B show an embodiment of a Corbino disc EOF pump integrated into a pipetting well. FIG. 6A shows a side view of the device while 6B shows a top view. Two parallel plates 61 and 62 with glass or silica surfaces, having spacer blocks 68 inserted between them in order to keep the sub-micrometer distance between them, is fastened at the bottom of a pipetting well 69 using a sealing adhesive 71. When an electrical ion current is drawn between the electrodes 63 and 64, the pumping action takes place in the liquid-filled space between the closely spaced plates 61 and 62. The upper electrode 63 can either be integrated into the pipetting well (as shown) or be dipped into well from a device holder above. The arrow 73 indicates the fluidic connection to the rest of the device. To prime the EOF pump, liquid should be pipetted into the well above the parallel plates. To overcome the capillary forces, gas pressure should be supplied on top of the well in order to force liquid out of the space between the plates, down to the lower electrode 64. As soon as the liquid touches both electrodes 63 and 64 the EOF pump is functional and can take over the pumping.

Figure 7B:
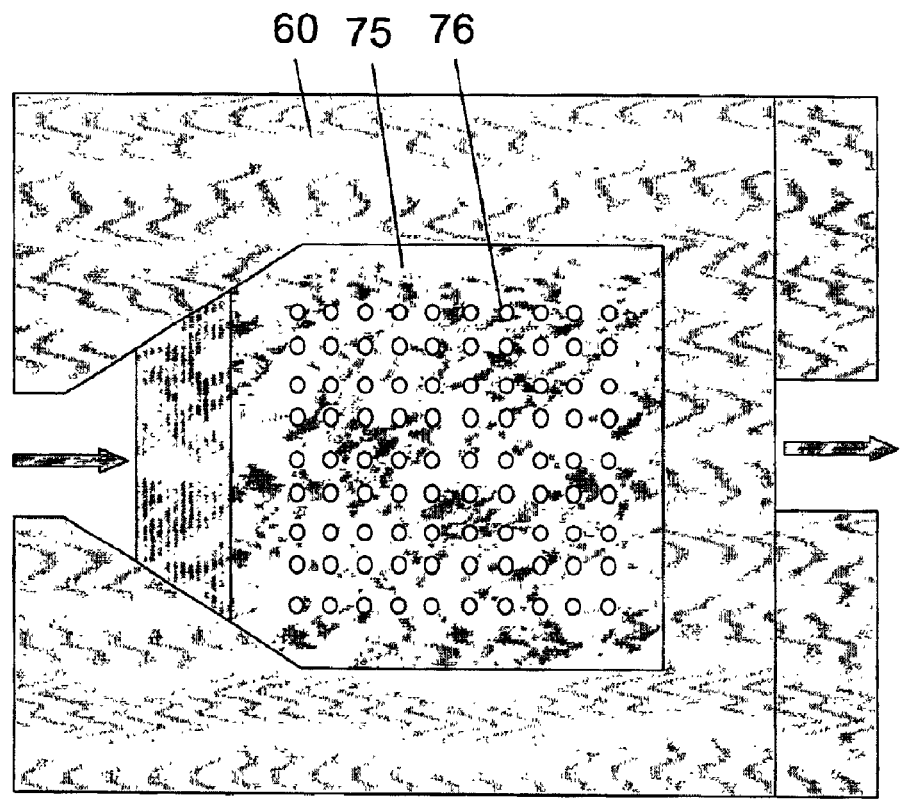

FIGS. 7A and B show an embodiment of a sieve based EOF pump. FIG. 7A shows a side view of the device while FIG. 7B shows a top view. A housing 60 contains a microstructured unit 74, having a thin membrane 75 on its top surface. The microstructure is fastened in the housing using a sealing adhesive 69. The membrane has a surface consisting of silica or glass. An array of holes 76 with diameters less than one micrometer penetrates the free-standing membrane in the centre of the microstructure. When an electrical ion current is drawn between the electrodes 63 and 64, the pumping action takes place in the immediate vicinity of the holes. The arrows indicate the liquid flow path.

Figure 6B:
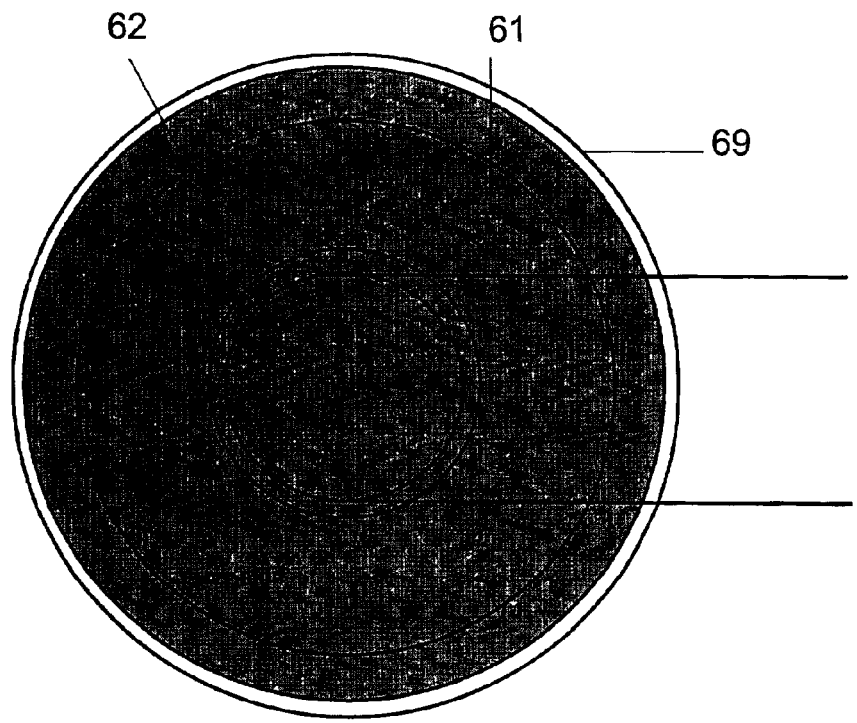
Figure 8:
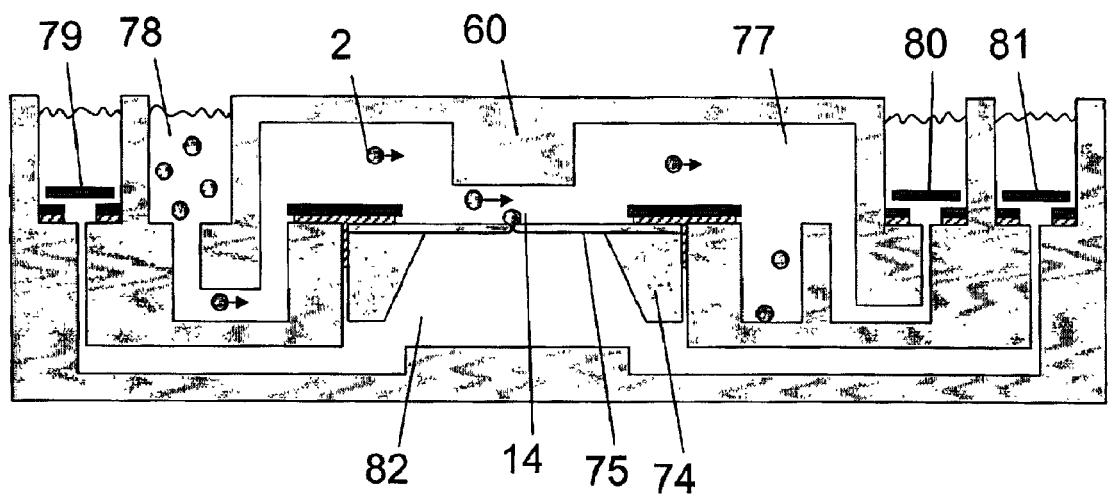
FIG. 8 is a cross sectional view of an embodiment of the present invention using the electroosmotic flow pump of FIGS. 6A and B.

FIG. 8 shows an embodiment of a substrate according to the present invention having the cell capture site together with liquid flow canals and three EOF pump sites. A housing 60 contains fluidic canals 77 an 78 separated by a microstructured unit 74 supporting a thin membrane 75 on its top surface. A passage in the membrane 75 is adapted to hold a cell 2 and forms the measurement site 14. The fluidic system consists of two separate flow systems. The first flow system consist of the canal 77 holding a cell solution. The canal 77 is in contact with the upper part of the membrane 75, an inlet 78 for adding the cell solution, and an outlet 80 with a corbino EOF pump (electrodes are not shown, but can be located as shown in FIGS. 6A and 6) for generating and controlling a flow in the cell solution in the canal 77. The second flow system consist of the canal 78 holding an intracellular buffer solution. The canal 78 is in contact with the upper part of the membrane 75, an inlet 79 and outlet 81 with Corbino EOF pumps (electrodes are not shown, but can be located as shown in FIGS. 6A and 6) for generating and controlling a flow in the buffer solution in the canal 78. Cells 2 are introduced through the inlet 78 acting as a pipetting well and are transported through the fluidic system to the measurement site 14. The canal is narrowed in the proximity of the cell capture site 14 in order to enable cell detection using the Coulter counter principle.

After having performed a measurement on a cell, the cells must be removed and the substrate can be cleansed either to be used again or to be disposed. In either case, all traces of cells and compounds should be properly removed. The cell can be removed and the canal and passage can be flushed using the electroosmotic flow. For this purpose, the flow will typically be as high as possible.

In electrophoresis, an electrical field will exert a force on a charged particle, the direction of the force depending on the direction of the field and the charge of the particle (positive or negative). By designing the working and reference electrodes to provide an electric field with the field lines converging at a site, charged particles such as cells and vesicles can be guided to the site using electrophoresis. It is important to realise that when performing electrophoresis, the electrical field acts on the individual particle or cell, whereas in electroosmosis, the field generates a flow in a bulk medium. Therefore, the detailed shape of the electrical field plays a more important role in electrophoresis than in electroosmosis.

In the embodiments described in relation to FIGS. 1B, 2B, and 3B, the reference electrode 8 at least partly encircles the site and/or the working electrode. A detailed description of electrophoresis will now be given referring to FIGS. 9A and B.

FIGS. 9A and B show side-views of a substrate 12 with working electrodes 16 at least partly encircled by a reference electrode 8. The working electrode is positioned in or below the passage 30 at the bottom of the well. Preferably, the regions of the site surrounding the working electrode are coated with a hydrophobic material 26 in order for cells not to stick to these regions.

Figure 9B:
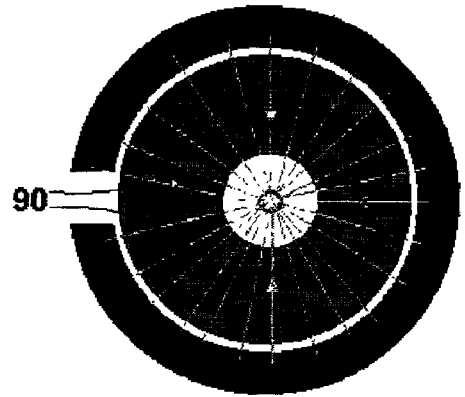

When an electrical potential difference is applied between electrodes 16 and 8, an electrical field having field lines 90 converging at the working electrode 16 is formed as shown in FIGS. 9A–B. Due to the geometry where the reference electrode 8 encircles the passage 30 or working electrode 16, all electrical field lines from the reference electrode 8 will be directed towards the working electrode 16 or alternatively the passage 30. Furthermore, at any position within the circumference of the reference electrode 8, the density of the field lines, and hence the strength of the electrical field, will increase in the direction towards the working electrode 16 or alternatively the passage 30. For the electric field lines to be directed towards the passage 30 in the embodiments of FIGS. 1A–B, 2A–C, and 3A–C, the working electrode 16 should be positioned nearby or in the passage 30.

In the embodiments described in relation to FIGS. 1B, 2B, and 3B, applied cells can be positioned at the working electrode 16 or alternatively the passage 30, by applying an electrical potential difference between electrodes 16 and 8. The potential needed for electrophoresis is typically larger than the potential needed in electroosmosis and will, depending upon the distances between electrodes 16 and 8, be on the order of several volts. The reference electrode 8 is typically large compared to a cell, typically this means that it has a diameter between 10 $\mu$m and 5 mm, preferably between 100 $\mu$m and 1000 $\mu$m.

In a preferred embodiment, the positioning is performed by at combination of the different described in the above.

Figure 11:
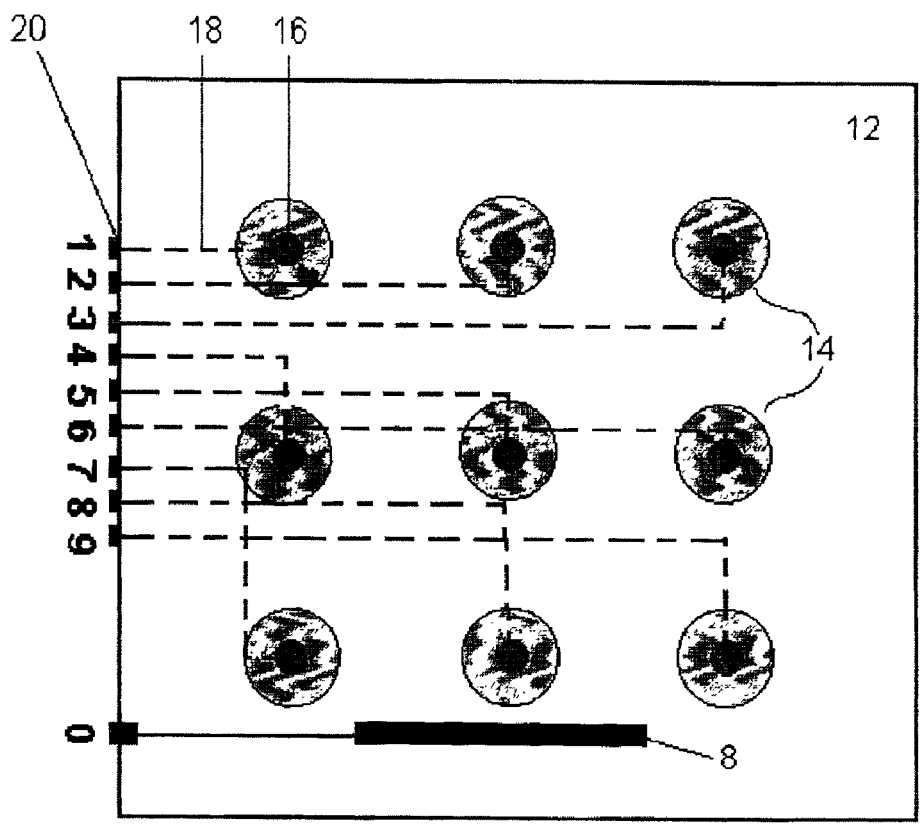
FIG. 11 shows an array of electrodes connected to a line of contacts.
Figure 12:
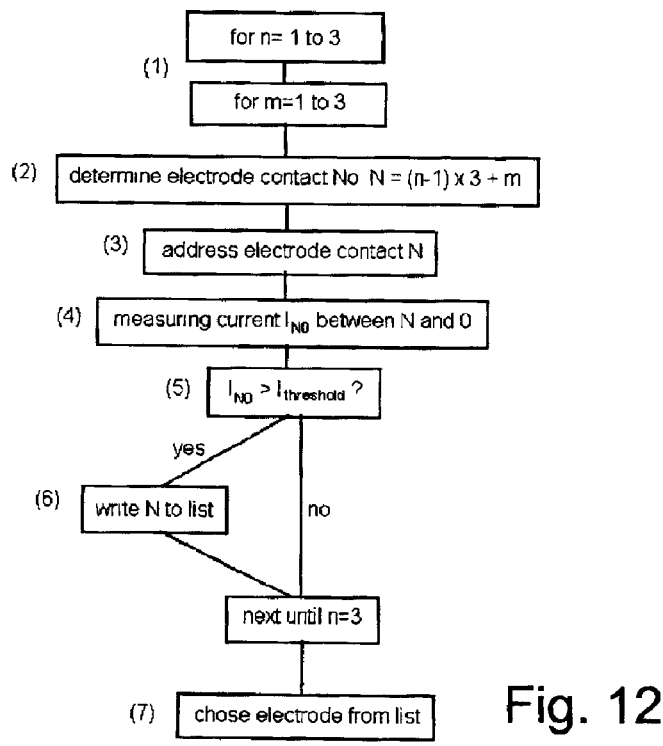
FIG. 12 shows a flow diagram of a procedure for detecting a cell forming a giga-seal with an electrode in the array of electrodes shown in FIG. 11.
Figure 13:
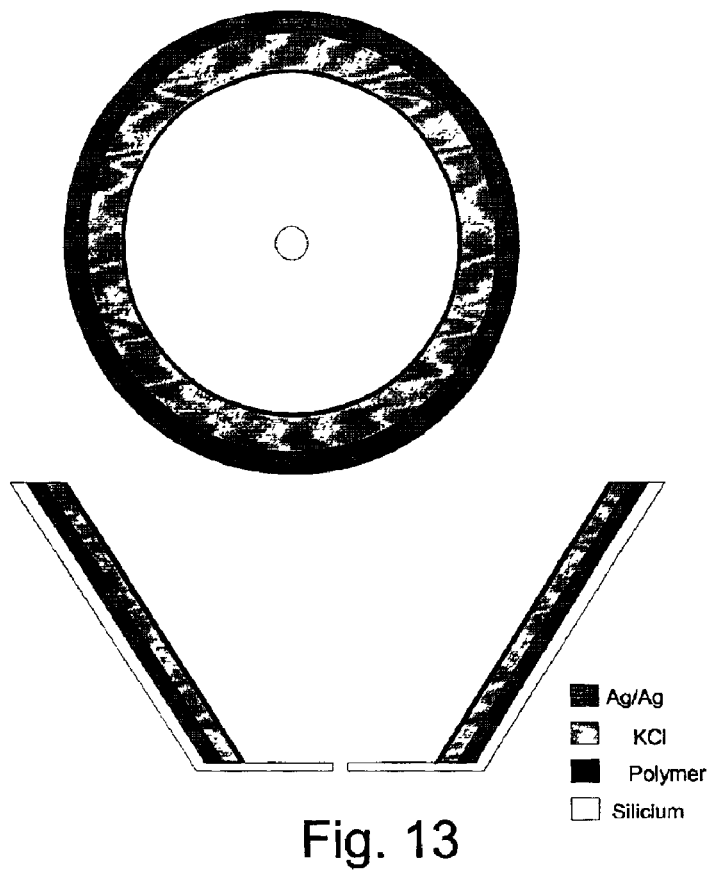
FIG. 13 shows an embodiment of a well according to any of the substrates shown in FIGS. 1A–B and 3A–C where the reference electrode has a bridge in order to avoid contamination of the liquid.

In order to detect whether a site has established a giga-seal to a cell, leak currents are measured between working and reference electrodes. Even though a test confinement 30 may include numerous electrodes, it is a simple task to search for electrodes isolated by giga-seals, a job well suited for a computer. FIGS. 11 and 12 propose a scheme for detecting giga sealed measuring sites. A detailed description of an embodiment of an electrical system for performing such scheme will be given later.

In FIG. 11, a number of sites form a nxm matrix (here 3×3). The electrode connections 18 lead to a line of contacts 20 (No. 1 to 9) on the substrate that can be individually addressed by a computer with means for measuring currents. A list of giga-sealed electrodes can be made using a simple method sketched in the flow diagram of FIG. 12. First (1), two loops are established for going through all entries in the matrix of electrodes. In (2), the n×m array of the matrix are unfolded to provide an individual addressing (3) of electrode contacts with an electrode contact number N (No. 1 to 9). A step function voltage is applied between contact N and the reference electrode 8, contact No. 0, the resulting current signal is measured (4), and the character of the seal (i.e. whether it is a giga-seal or not) can be determined by the size of the resulting current, since a large leak current will flow is there is no giga-seal $|_{NO}>|_{threshold}$, whereas only a smaller current will be drawn through the cell if a giga seal is established. If a giga-seal is detected, the contact number is added to a list of suitable electrodes (6) from which a working electrode is selected (7). This scheme carries some information of the relative positions n,m of suitable electrodes. This information can be used for selecting the optimal working electrode in (7), but can be omitted so that each electrode is simply known by its contact number N. Typically, only one electrode per test confinement is chosen.

The activity of these channels can be measured electrically in a single channel recording (on-cell recording) or the patch can be ruptured allowing for electrical measurements of the channel activity of the entire cell membrane (whole-cell recording). High-conductance access to the cell interior for performing whole-cell measurements can be obtained in at least 3 different ways:

a) In the substrate embodiment described in relation to FIGS. 1A–B, 2A–C, 3A–C, and 8, the membrane can be ruptured by suction from the backside of the substrate. Negative hydrostatic pressures are applied either as short pulses of increasing strength or as ramps or steps of increasing strength pressures should be between 10 and 200 mBar. Membrane rupture is detected by highly increased capacitative current spikes (reflecting the total cell membrane capacitance) in response to a given voltage test pulse. The suction may be provided by the same methods as the suction for positioning cells, or of any combination of those.

b) Membrane zapping by applied voltage pulses. Voltage pulses are applied either as short pulses of increasing strength (200 mV to 1 V) and duration (10 $\mu$sec to 1 sec), or as ramps or steps of increasing strength, between the electrodes. The lipids forming the membrane of a typical cell will be influenced by the large electrical field strength from the voltage pulses, whereby the membrane disintegrates in the vicinity of the electrode. Membrane rupture is detected by highly increased capacitative current spikes in response to a given voltage test pulse. A detailed description of an embodiment of an electrical system for applying such ramped pulses will be given later.

c) Permeabilization of membrane. Application of pore forming compounds (for example antibiotics such as nystatin or amphotericin B), by e.g. prior deposition of these at the site. Rather than by rupturing the membrane, the membrane resistance is selectively lowered by incorporations of permeabilizing molecules, resulting in effective cell voltage control via the electrode pair. The incorporation is followed by a gradually decreasing total resistance and an increasing capacitance.

The electrophysiological measurements to be performed using the system of the present invention comprises transmitting a current between two electrodes immersed in a liquid, involving electrolytic reactions at each electrode. When designing the system, a series of issues arises which are primarily due to the very small scale of the individual test confinements.

According to the present invention, the substrate holding the measuring sites and electrodes is a microstructure and hence the size of the electrodes can be minimised as well. One important aspect when considering the electrodes is to determine the necessary size of the electrodes. In the electrode reactions, the metal of one of the electrodes slowly dissolves and the electrode will eventually dissolve completely. This issue has not been relevant in the prior art since electrodes have always been too large for the effect to be noticeable, unless carried out over a long period of time. Also, since the substrates according to the present invention preferably are disposable mass productions, the material costs as well as potential contamination after disposal should be kept at a minimum.

In long experiments, the experimenter is to carry out an experiment with e.g. 10 nA current for 10 minutes and the electrode must contain a certain amount of AgCl in order to be able to run the electrode process:

$AgCl \rightarrow e^- + Ag(s) + Cl^-(aq)$

From Faradays constant (96485.3 C mol$^{-1}$) we obtain the number of moles n of AgCl that equals a current of 10 nA for 1 second since Ampere is defined as C s$^{-1}$:

$n = 10^{-8}$ C mol/96485.3 C $s = 1.0364 \cdot 10^{-13}$ mol $s^{-1}$, which means that the number of moles N required to run the experiment for 10 minutes is:

$N = 600$ $s \cdot 1.0364 \cdot 10^{-13}$ mol $s^{-1} = 6.22 \cdot 10^{-11}$ mol.

The density of AgCl is 5.589 g/cm$^3$ and the molecular weight is 143.321 g/mol. We therefore get that $6.22 \cdot 10^{-11}$ mol equals (143.321 g/mol$\cdot 6.22 \cdot 10^{-11}$ mol)=$8.91 \cdot 10^{-9}$ g of AgCl. This amount has the volume:

$V = 8.91 \cdot 10^{-9}$ g/5.589 g/cm$^3 = 1.595 \cdot 10^{-9}$ cm$^3 = 1595$ $\mu$m$^3$.

In more general terms, this means that we need 15.95 $\mu$m$^3$ AgCl per nA per minute that the current flows.

In the case that current runs in the opposite direction we have the following electrode reaction:

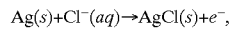
$Ag(s) + Cl^-(aq) \rightarrow AgCl(s) + e^-$, which describes the conversion of Ag into AgCl and the electrode must therefore contain Ag otherwise the current cannot run in the opposite direction and we get the possibility for the following toxic electrode reaction:

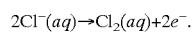
$2Cl^-(aq) \rightarrow Cl_2(aq) + 2e^-$.

Another possible reaction, with a concomitant change in pH is:

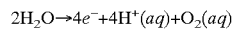
$2H_2O \rightarrow 4e^- + 4H^+(aq) + O_2(aq)$

Ag has a density of 10.3 g/cm$^3$ and a molecular weight of 107.9 g/mol. Using the example with 10 nA for 10 minutes we get (107.9 g/mol$\cdot 6.22 \cdot 10^{-11}$ mol)=$6.71 \cdot 10^9$ g of Ag. This amount has the volume of 650 $\mu$m$^3$.

The total volume of the Ag/AgCl electrode used for the extreme case of current measurement is therefore:

$V_{total} = 650 + 1590 = 2240$ $\mu$m$^3$.

In general terms, this means that we need 22.4 $\mu$m$^3$ Ag/AgCl per nA per minute that the current flows.

Long measurements are, as mentioned above, only needed in studies of slowly inactivating currents such as described by Smith and Ashford where the currents inactivate over several minutes. In the majority of studies, the electrodes would need an Ag/AgCl deposit in the range of 1–20 $\mu$m$^3$. A possible confiuration of the electrodes is illustrated in FIG.

13 where the KCl and Ag/AgCl deposit is formed on the side walls of a well. Ag/AgCl electrodes should be stored in 0.9% NaCl to obtain minimal drift.

Ref.: Smith M A, Ashford M L. Inactivation of large-conductance, calcium-activated potassium channels in rat cortical neurones. Neuroscience 2000; 95(1): 33–50

It is important that the activity of Cl$^-$ is the same at both Ag/AgCl electrodes otherwise it can lead to large offset currents running between the two electrodes. A way to keep the activity of Cl permanent is to separate the Ag/AgCl from the recording bath with a high molarity KCl bridge. An elimination of Cl results in a totally polarised electrode with build-ups of potentials causing other unwanted electrode reactions such as toxic gas building and pH changes.

Ref.: Raynauld J P, Laviolette J R The silver-silver chloride electrode: a possible generator of offset voltages and currents. J Neurosci Methods 1987 Mar.; 19(3): 249–55

Ag/AgCl electrodes can lead to contamination of biological samples with Ag and it is therefore advisable to shield the biological specimen from direct contact with the Ag/AgCl electrode. This can be achieved by using high molar KCl bridge between the Ag/AgCl and the compartment containing the biological specimen. A bridge can be established by coating the substrate material first with Ag/AgCl followed by a KCl crystal coating and then encapsulating with a polymer. The polymer is ruptured at certain locations with a laser or using photolithography, allowing electrical contact to the compartment containing the biological specimen.

The electrical potential of an electrode measured against a reference electrode when there is no current flowing trough the electrode. In other words, the electromotive force of an electrochemical cell consisting of the electrode in question and a reference electrode. See also equilibrium and standard electrode potential. The concept of equilibrium potential is probably easiest to demonstrate with a simple metal/metal-ion electrode system. When a metal (e.g., silver) is immersed in a solution containing its ion (e.g., silver nitrate solution) metal ions will cross the metal/solution interface. They will pass from the phase where the "chemical energy" of the ion is large to the phase where the "chemical energy" of the ion is smaller. Depending on the system, this can occur in either direction. However only the positively charged (e.g., silver) cations can pass through the interface. The negatively charged electrons cannot pass into the solution, and the anions (e.g., nitrate) cannot pass into the metal.

When having an electrode in an ionic solution, a number of polarisation effects will occur:

1. Activation polarisation (found at the electrode interface of Ag/AgCl electrode) can be neglected for Cl containing solutions, but it can become a considerable problem in Cl free solutions. This influences the activation potential of the electrodes, but can be avoided using a KCl bridge as described under Contamination.
2. Concentration polarisation (found in the depletion zone up to some hundreds of micrometers). This introduces a contamination of the liquid by depletion of ions from the electrode. The electrodes have to be positioned sufficiently away from the bulk solution not to cause interference with the concentration profile of the bulk, typically, distances of the order of 200 μm are sufficient.
3. Ohmic polarisation (reflects the resistance of the entire electrochemical cell) and gives rise to an IR drop. This introduces en extra series resistance in the measuring circuit which depends upon the current, and thereby introduces an error in the measurement which has to be corrected. To minimise the effect, the distance between the working electrode and the reference electrode should be minimised. Together with the capacitance of the double layer of the electrode this sets the time constant of the electrode response. This will therefore determine the maximal frequency that can be recorded with the electrodes in the given situation.

Ref.: Tassinary L. G., Geen T. R., Cacioppo J. T., Edelberg R Issues in biometrics: offset potentials and the electrical stability of Ag/AgCl electrodes. Psychophysiology 1990 Mar.; 27(2): 236–42

Figure 14:
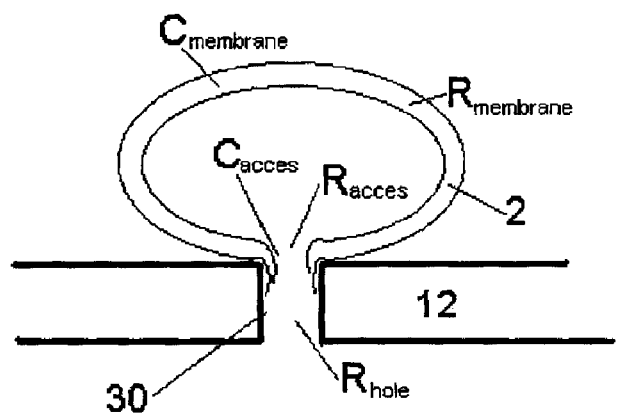
FIG. 14 is a close-up of a patch clamped cell showing various electrical parameters of a measuring configuration.

Having established an applicable measuring configuration, the giga-sealed cell forms part of the electrical system. FIG. 14 is a close up of a measuring configuration showing the total electrical resistance $R_{series}$ and a fast and slow capacitance, $C_{fast}$ and $C_{slow}$ of the measuring configuration comprising a cell 2, and the substrate 12 with passage 30.

Electrical System

The electrical system for measuring of electrical properties of membranes on the substrate, hereafter the main circuit, comprises one or more working electrodes present at each measuring site and a reference electrode in contact with each site.

Each pair of working-reference electrodes is connected to one or more amplifiers and a low noise current to voltage converter. Since the substrate according to the present invention comprises a large number of measuring sites, the amplified outputs (typically in sets of 8 or more) are lead to a multiplexer which on turn passes each signal to a digital signal processor (DSP) through an analogue to digital converter (A/D). The DSP is responsible for the pre-analysis of the signals and for the interface to a computer. The DSP is responsible for processing of the incoming signals and can be used for rapid calculations of polynomial—as well as Fourier coefficients for simple mathematical description of the signals. Further data processing is typically performed in a computer. The main circuit is also responsible for generating voltage clamp signals and test signals to each measuring site.

In the following sections, the main circuit is described in relation to FIG. 15, which shows an overview of the main circuit. Thereafter, a detailed description of different parts of the main circuit is described in relation to FIGS. 16 to 20.

To measure a current signal from a given cell 101 in a voltage clamp configuration, the electric potential between the working electrode and the reference electrode can be switched on/off using an analogue switch 103. Thereby different cells/sites can be addressed using enable pins D1–D4 on an enable network 110. A current signal in the working electrode is converted directly to a voltage signal in a current-to-voltage (I-V) converter 102.

The I-V converter function is divided in two parts, 102 and 104. The analogue switch 103 and I-V converter 102 can be physically placed on the substrate. I-V converter 104 and forward is preferably placed on a second substrate. In the illustrated embodiment, one well contains 4 sets of analogue switches 103 and I-V Converters 102, each connected to an I-V Converter 104 outside the well. Only one set is selected at a time by enable network 110 on the enable pin D1–D4.

The output signal from the I-V conversion passes trough a differential amplifier 105 and a low-pass filter 106, in order to cut off any signal with a frequency above 10 kHz. The filtered signal is fed to a Sample Logic 107 and feedback network 108 corresponding to the enable pins D1–D4.

There must be one feedback network 108 for each set of I-V converters to keep the $V_{ref}$ voltage stable, in regard to clamp cells 101. The feedback network 108 consists of I-V conversion feedback, a fixed series resistance compensation, and a hold- and stimulate-voltage $V_{stim}$. All this is fed back by the signal pin $V_{ref}$. The feedback network 108 is controlled by the enable network 110 on enable pin D1–D4.

Figure 15:
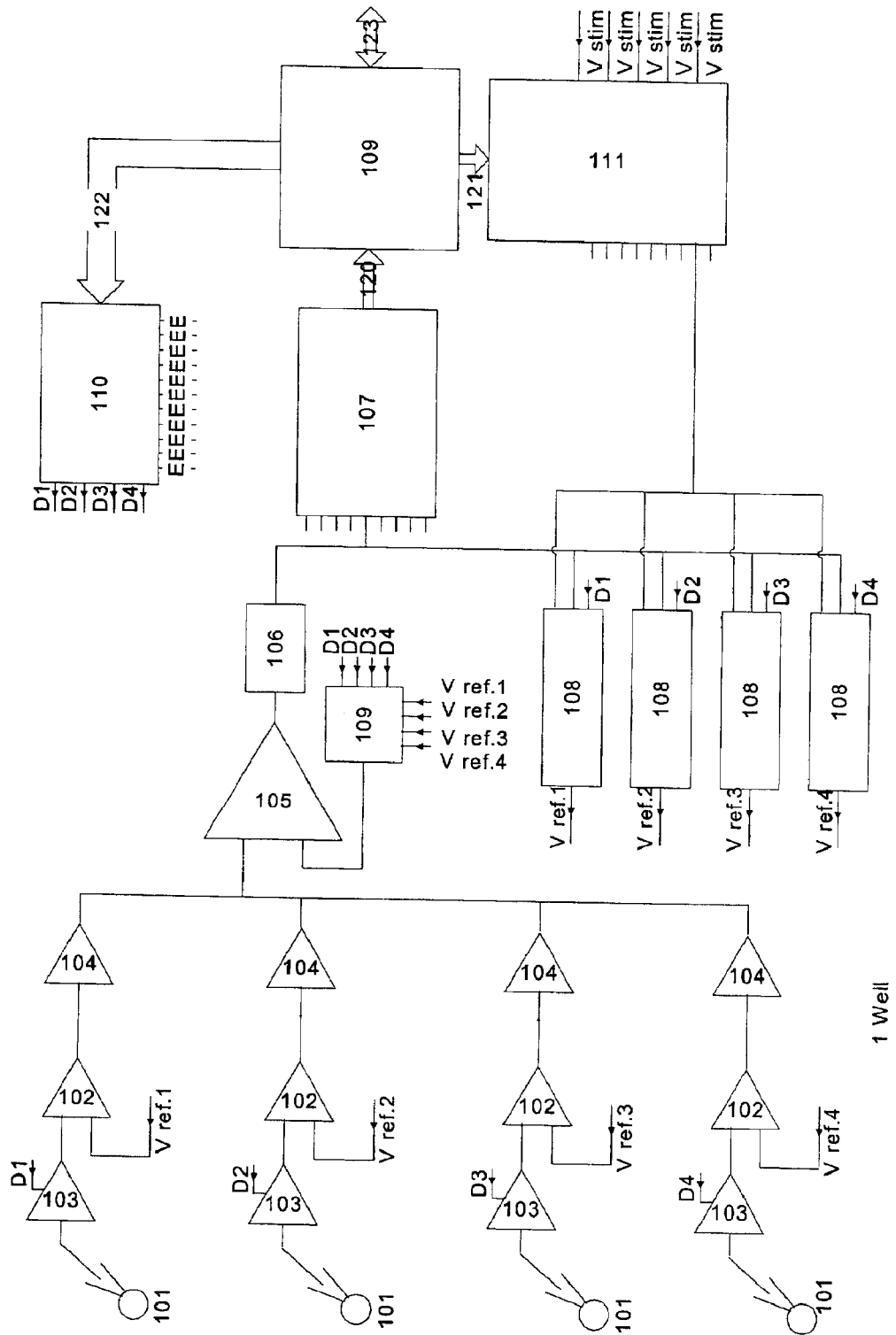
FIG. 15 is an electrical circuit diagram showing an electrical system (main circuit) for measuring of electrical properties of membranes on a substrate according to a preferred embodiment.

Also in FIG. 15, an analogue switch 109 ensure that the correct $V_{ref}$ is provided to the differential amplifier 105, by means of the enable pins D1–D4, which are controlled by the enable network 110.

The sample logic 107 shown in the main circuit in FIG. 15 converts the amplified and filtered analogue signal into a digital signal. The digital signal is forwarded, via data bus 120, to the processor DSP/CPU 109. In the DSP/CPU 109 the digital signal/data can be converted to a polynomial expression. From the DSP/CPU 109 the data is forwarded, via the PC-interface 123 to a computer. The DSP/CPU 109 keeps track of which channel and which well is selected by sending out an address, via the address bus 122, to the enable network 110. This address is decoded in the enable network 110 and the chosen cannel is selected on pins D1–D4 and the enable pins E. The DSP/CPU 109 may also be able to apply an analogue signal to each I-V converter 102, by sending a digital signal, via the data bus 121, to a stimulate signal generator 111. The stimulate signal generator 111 converts the digital signal to an analogue signal.

Figure 16:
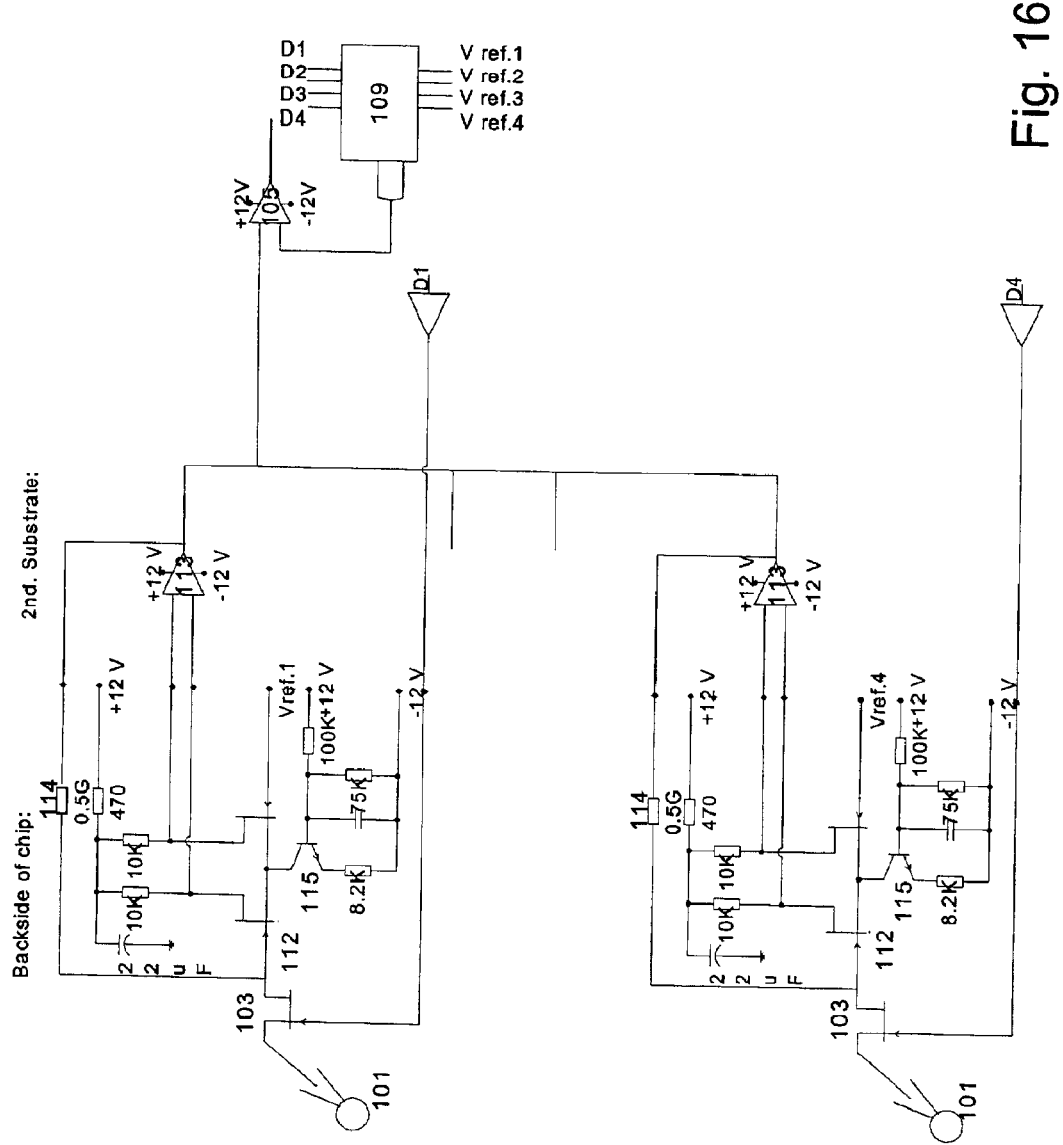
FIGS. 16 and 17 are electrical circuit diagrams showing different embodiments of a current-to-voltage converter parts of the circuit of FIG. 15.
Figure 20:
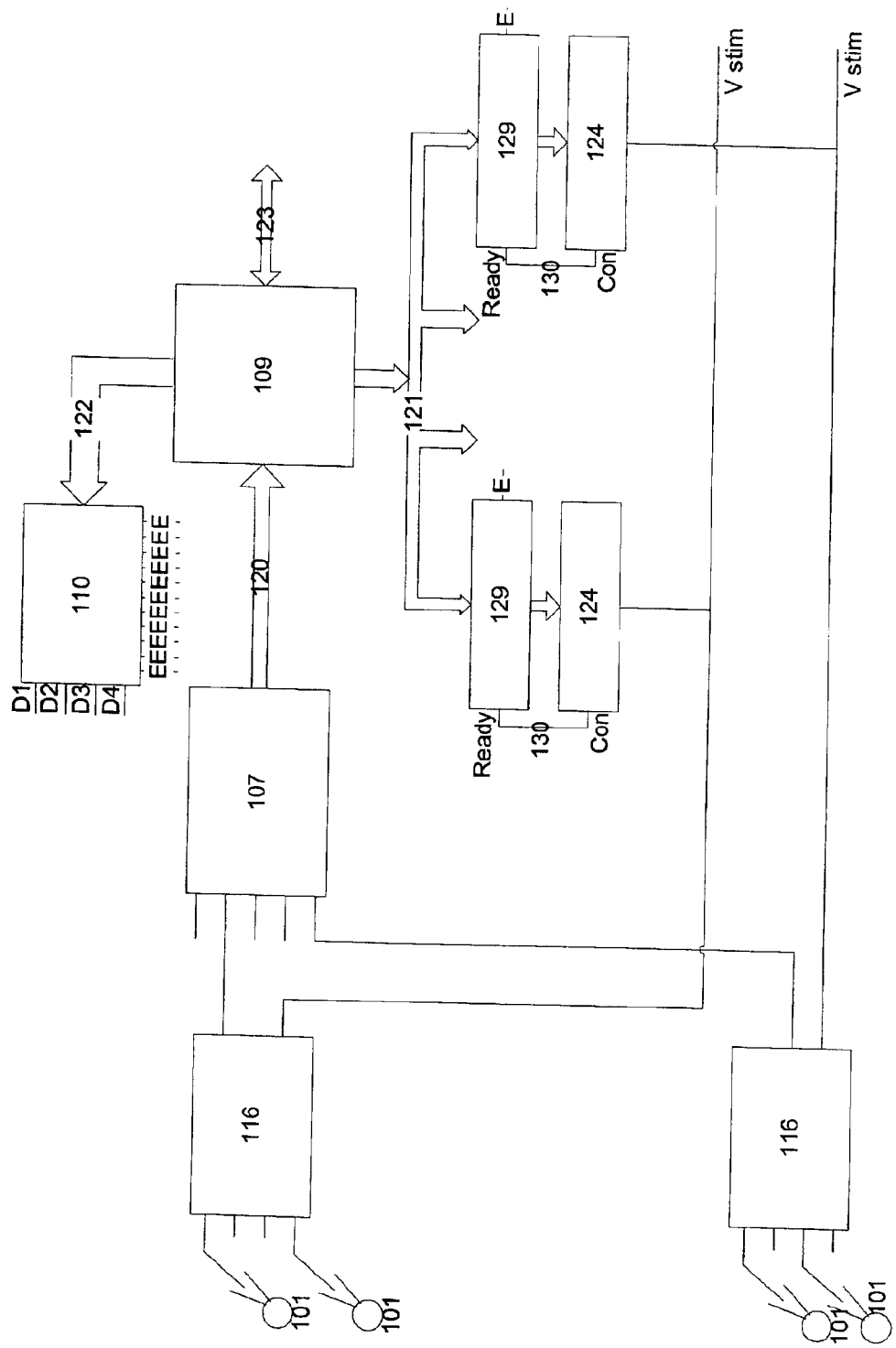

FIGS. 16 and 20 show different embodiments of the I-V converter parts, 102 and 104, of the main circuit of FIG. 15. FIGS. 16 and 20 illustrate the electronic circuits of two measuring sites, however, a larger number of I-V converter parts can be provided in parallel.

In FIG. 16, the measured current signal from the selected analogue switch 103 is send to one of the inputs of a dual FET U430 112. The dual FET U430 112 is working as a differential preamplifier, the output of which is amplified further by a conventional op-amp NE5534 113. A second input of the dual FET U430 112 is used to receive the $V_{ref}$ feedback. $V_{ref}$ is a signal composed by the feedback network 108. $V_{ref}$ is composed by many different signals, such as $V_{stim}$, a feedback voltage and a fixed $R_{serie}$ compensation voltage. The imposed voltage level on $V_{ref}$ on the differential preamplifier will force the level at the other input on the differential preamplifier to be the same and hence assert the correct voltage clamping of the cell.

The transistor network 115 is a "constant current" configuration. It keeps the DC working voltage of the differential preamplifier in place and secondly but not least, it improves the common mode rejection of the differential preamplifier. The dual FET U430 112 functions as a differential preamplifier, and op-amp NE5534 113 can be considered a "super op-amp" configured as a current to voltage converter. The conversion is performed through the feedback resistor 114 according to the formula $V_p=I_p*R_f$, where $R_f$ is the resistance of the feedback resistor 114, typically of the order 0,5 GΩ. A differential amplifier 105 is used to read out the voltage difference.

The main advantage of this circuit, is that the dual FET U430 112 and the analogue switch 103 can be implanted on the backside of the substrate, actually the FET's may be manufactured directly in a silicon layer. Another advantage of this circuit is that it is possible to achieve better specifications when using the described components.

Figure 17:
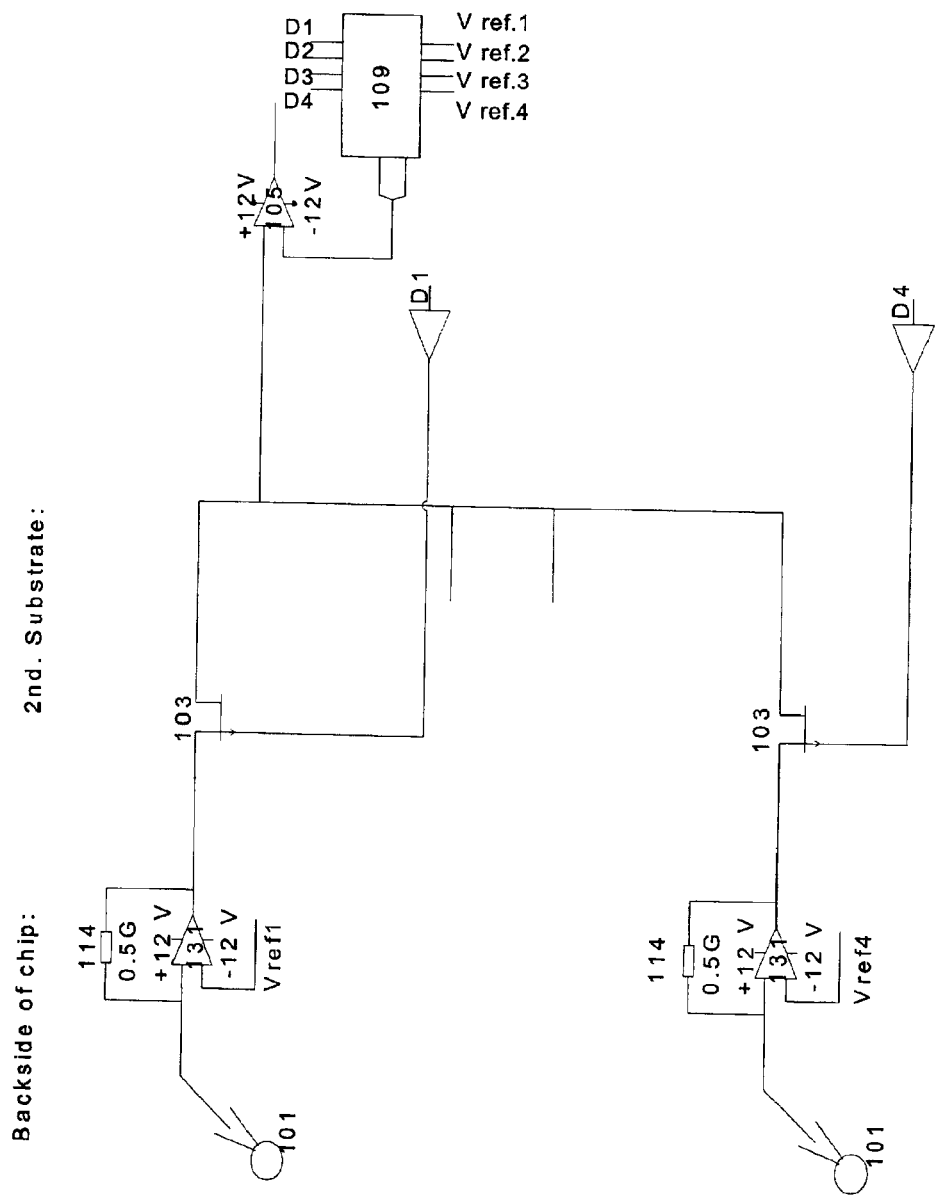

The schematic circuit described in the previous sections is only one example of how the I-V converter could be constructed. Another example is illustrated in FIG. 17. Here, the dual FET U430 112 and the NE5534 113, are exchanged with one op-amp AD 743 131, and the I-V Converter and the analogue switch 103 are positioned in reverse order. The main advantages of this circuit are that it uses fewer components and allows for the use of "flip chip" mounting technology.

Figure 18:
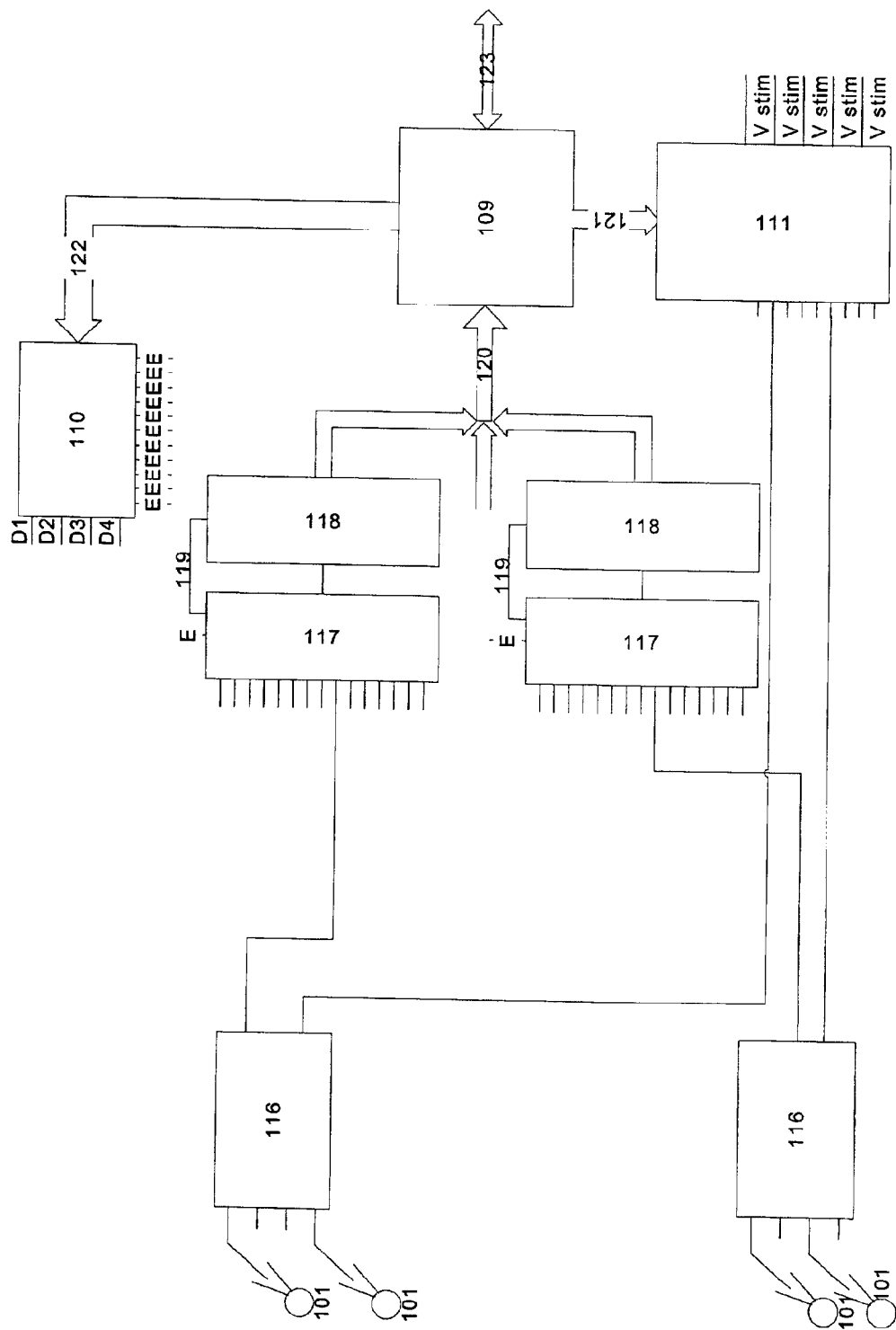
FIG. 18 is an electrical circuit diagram showing a sample logic parts of the circuit of FIG. 15, for receiving, multiplexing and converting signals from different measuring sites.

FIG. 18 shows an embodiment of the sample logic part 107 of the main circuit of FIG. 15.

The signals from front-end amplifiers 116, such as the signal provided from the parts 102–106 in FIG. 15, are multiplexed in the MUX 117 to the analogue to digital converter 118.

The sample rate of the analogue to digital converter 118 must be at least two times higher than the maximum frequency of the input signal (in order to fulfil the Nyquist "sample theorem"). In this case, the analogue signal has been through a 10 kHz low pass filter, hence the sample rate must be at least 20 kHz or better 30 kHz, to get the right information in the digital signal. Also, the sample rate should be multiplied by the number of inputs on each MUX 117. After the conversion of the analogue signal to a digital signal, the DSP/CPU 109 may make additional signal treatment, for example, convert the data to a polynomial.

Each multiplexer 117 is enabled on the E pin by the enable network 110. There is a "MUX READY" connection 119 from the MUX 117 to the "A/D conversion begin" on the A/D converter 118. The digital signal goes via the data bus 120 from the A/D converter to the DSP/CPU 109.

Figure 19:
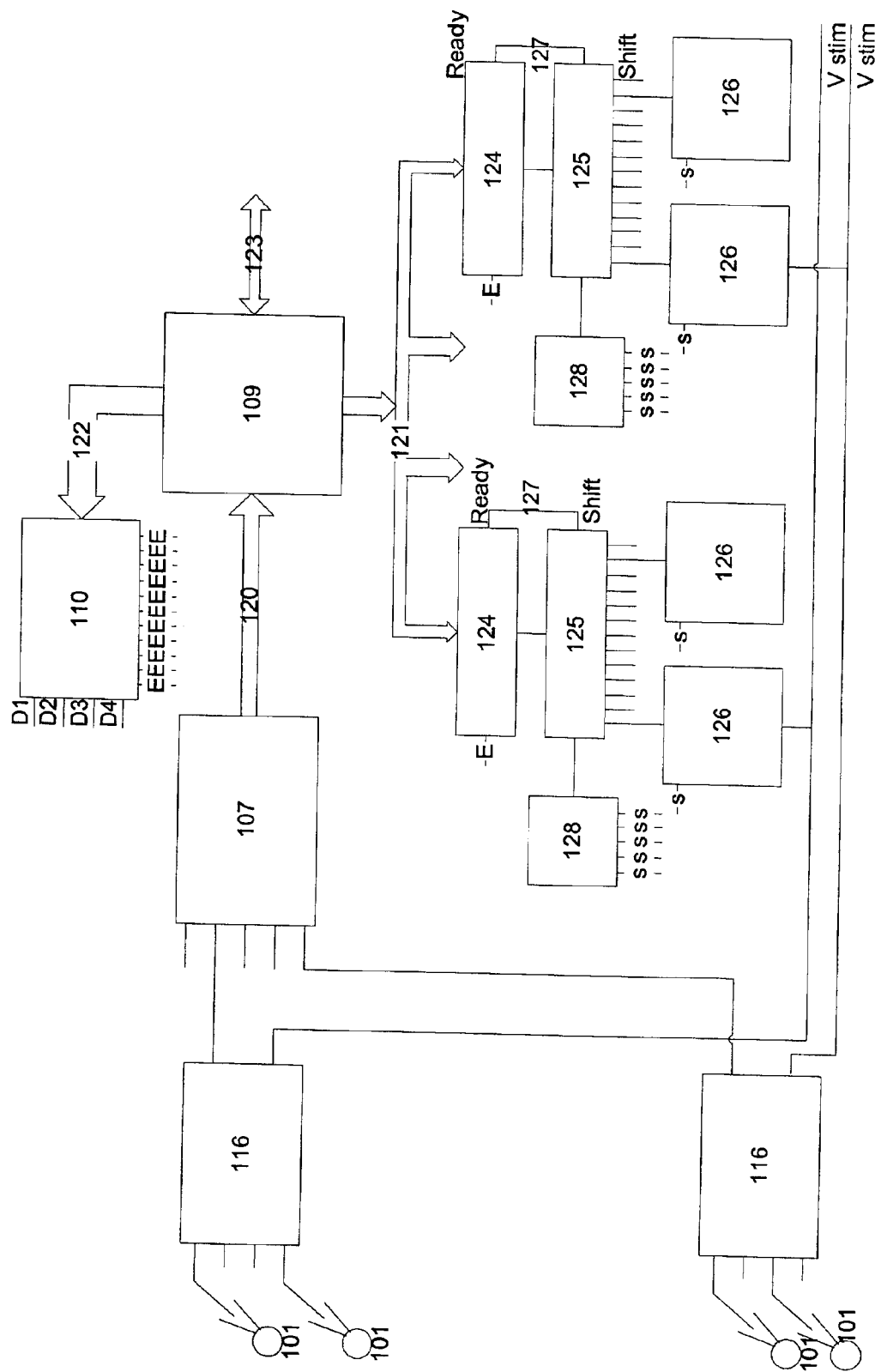
FIGS. 19 and 20 are electrical circuit diagrams showing different embodiments of a stimulation signal generator of the circuit of FIG. 15, for generating testing signals to the measuring sites.

FIGS. 19 and 20 show different embodiments of the stimulate signal generator part 111 of the main circuit of FIG. 15.

In the circuit shown in FIG. 19, the DSP/CPU 109 is able to provide an analogue signal to each I-V converter 116 ($V_{ref}$), by sending a digital signal, via the data bus 121, to the digital to analogue (D-A) converter 124 of the stimulate signal generator. This analogue signal is necessary for testing and or rupturing the patched cell 101 after a pre-programmed protocol in the DSP/CPU 109. The analogue signal may look like a ramp to stimulate the cell 101. The data bus 121 of the circuit in FIG. 19 allows the protocol to test four individual cells 101 in parallel, although only two ramp-generating circuits are shown. To generate a ramped analogue signal a series of different analogue signals is needed, but for the sake of the cell 101, these signals have to be applied in real time.

The digital to analogue converter 124 can generate one signal at the time, and in order to limit the number of digital to analogue converters 124, the analogue signal is passed trough a multiplexing unit 125 to a sample and hold circuit 126. The sample and hold circuit 126 operates as the words say: first it takes a "sample"-voltage measurement of the signal from the multiplexing unit 125, then it "holds" this "sample"-voltage measurement, while the multiplexing unit 125 is providing another analogue signal to another sample and hold circuit 126, etc. The digital to analogue converter 124 sends a "ready" signal 127 to the multiplexing unit 125, when the conversion is finished, after which the signals are released in a ramped sequence. The select network 128 keeps track of which sample and hold circuits 126 the multiplexing unit 125 is sending analogue signals to.

Another way of providing many different real time analogue signals at the same time, is to have sets of one latch 129 and one or more D-A converters 124, for each different type of analogue signal. This is shown in FIG. 20. The latch 129 passes the digital signal data from the data bus 121 through to the D-A converter when enabled on the enable pin E by the enable network 110 and holds this signal until a new digital signal is passed. The latch 129 sends a "ready" signal 130 to the digital to analogue converter 124, when the digital data is ready to be converted. If all the analogue signals look the same, which happens if all the cells 101 are exposed to the same test-signal, only one analogue converter 124 is needed.

Figure 21:
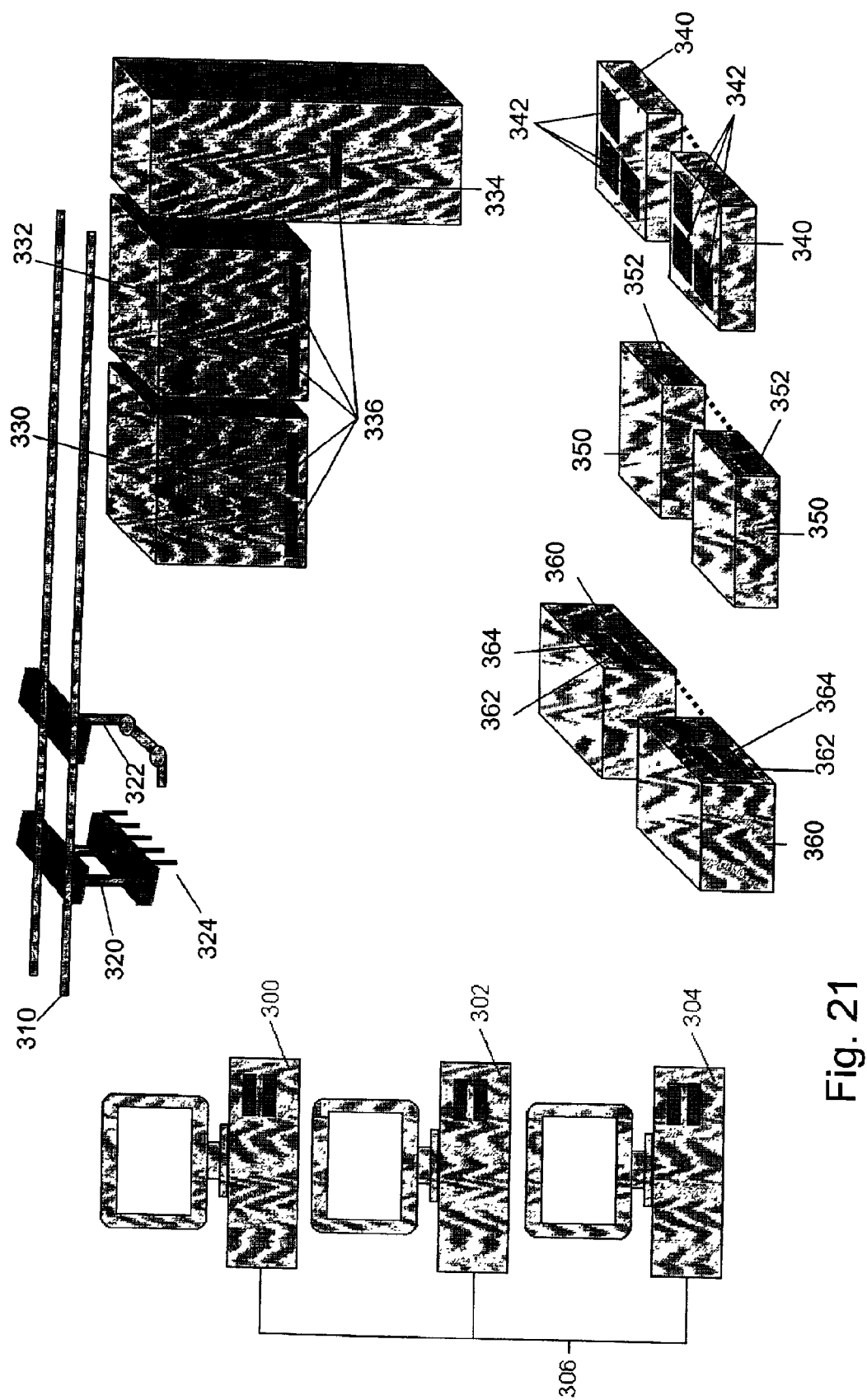
FIG. 21 shows an overview of a system according to the present invention.

FIG. 21 shows an overview of a system according to the present invention. In the following paragraphs, a shorthand description of the system will be given using the following references to FIG. 21:

| | | | |
|---|---|---|---|
| 300 | Server PC for communication & data collection | 334 | Compound storage and registration unit |
| 302 | Workstation PC for data acquisition & analysis | 336 | In- and out-put slots |
| 304 | Workstation PC for equipment control | 340 | Pipetting deck |
| 306 | High-speed communication network | 342 | Pipetting sites |
| 310 | Rails for robot arms | 350 | Cell application & positioning unit |
| 320 | Robot arm for pipetting | 352 | In- and out-put slots |
| 322 | Robot arm for plate handling | 360 | Compound application & electrical signal measurement unit |
| 324 | Array of pipettes | 362 | In- and out-put slot for compound plates |
| 330 | Cell incubator (Temp. & $CO_2$ control) unit | 364 | In- and out-put slot for "substrate" plates |
| 332 | Disposable storage unit | | |

FIG. 21 shows one of several possible solutions for carrying out the cell-, compound- and disposable handling necessary in a HTS system as well as the data acquisition, analysis and storage means necessary for the particular HTS patch-clamp application.

In FIG. 21, a server PC 300 is used for storage of experiment data being collected and send by one or more data acquisition and analysis workstation PCs 302, and for forwarding of inter-process communication and synchronisation messages between the different software components executing on the different PCs 300, 302 and 304. Data and messages are sent via a high-speed communication network 306.

One or more equipment control Workstation PCs 304 are used for controlling the robot arms 320 and 322, the cell incubator unit 330, the disposable storage unit 332, the compound storage unit 334 and the cell application and positioning unit 350. The pipetting deck 340, the pipetting sites 342 and the rails for the robot arms 310 can be viewed as a core of any commercially available HTS pipetting system. The robot pipetting arm 320 is used for liquid pipetting and may be loaded with permanent or disposable pipettes 324.

The robot plate handling arm 322 is used for fetching and carrying the disposables (compound carrier plates and experimentation plates (substrates)) from the disposable storage unit 332; for fetching and carrying cell-containing plates from the cell incubator unit 330 and for fetching and carrying compound-containing plates from the compound storage unit 334—all via the appropriate in- and out-put slots 336 to the relevant plate sites 342 and in- and out-put slots 352, 362 and 364.

In the cell application and positioning unit 350, cells are applied to the test sites on the experimentation plates (substrates) and are further positioned using one of the positioning means described elsewhere. When cells have been applied and positioned, the experimentation plate (substrate) is brought into the compound application and measurement unit 360, in which the experiments are conducted.

Depending on the cell positioning method used, the cell application and positioning unit 350, or its functionality, can advantageously be integrated into the compound and measurement unit 360.

Depending on the specific shaping of the substrate with electrodes, the adding of supporting liquid, cells and test compound can be carried out in several ways.

Cells may be stored in suspension in an incubator allowing for optimal (temperature and $CO_2$ level) storage conditions. Cells can be fetched from the incubator and injected into the flow system of the substrate, possibly using the same application equipment as will be described for compound application in relation to FIGS. 22 to 24. The cell positioning means are as described in the section about substrates.

Cells may also be cultivated directly on the substrate, while immersed in growth medium. In the optimal case, the cells will form a homogeneous monolayer (depending on the type of cells to be grown) on the entire surface, except at regions where the surface intentionally is made unsuitable for cell growth. The success of cultivation of cells on the substrate depends strongly on the substrate material.

Also, an artificial membrane with incorporated ion channels can be used instead of a cell. Such artificial membrane can be created from a saturated solution of lipids, by positioning a small lump of lipid over a passage. This technique is thoroughly described in e.g. "Ion Channel Reconstitution" by Christopher Miller, *Plenum* 1986, p. 577. If the passage size is appropriate, and a polar liquid such as water is present on both sides of the passage, a lipid bilayer can form over the passage. The next step is to incorporate a protein ion channel into the bilayer. This can be achieved by supplying lipid vesicles with incorporated ion channels on one side of the bilayer. The vesicles can be drawn to fusion with the bilayer by e.g. osmotic gradients, whereby the ion channels are incorporated into the bilayer.

Substrate exchange can be carried out by using wafers of a size that can fit within the dimensions of standard micro-titer plates which can then be mounted in a holding device of the size of standard micro-titer plates thus allowing for existing robotics to be used. Alternatively, a loading device based on existing technology for wafer inspection (typically used in connection with microscopy equipment) can be used.

Compounds to be tested can be stored in existing "hotels" available in connection with standard robotics equipment. Plate and compound registration can be based on reading of barcodes using existing equipment.

In the following, a number of different schemes for compound application are described.

Figure 22A:
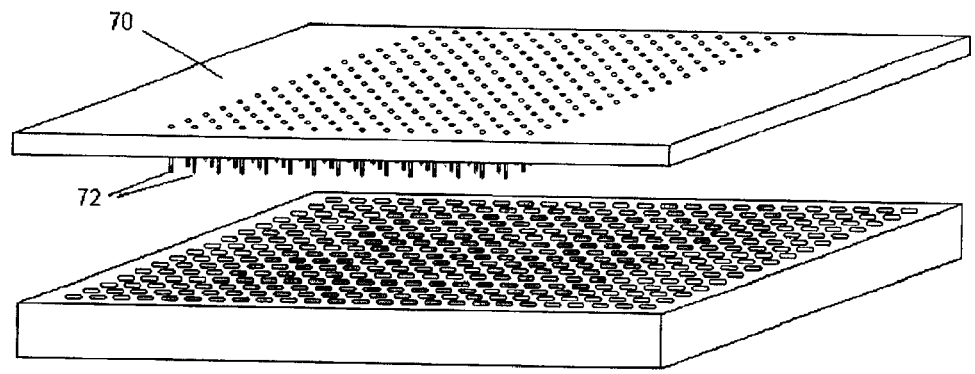
FIGS. 22A and B, 23A and B, and 24A–C show different embodiments for pipetting carrier and compounds to the substrates according to the present invention.
Figure 22B:
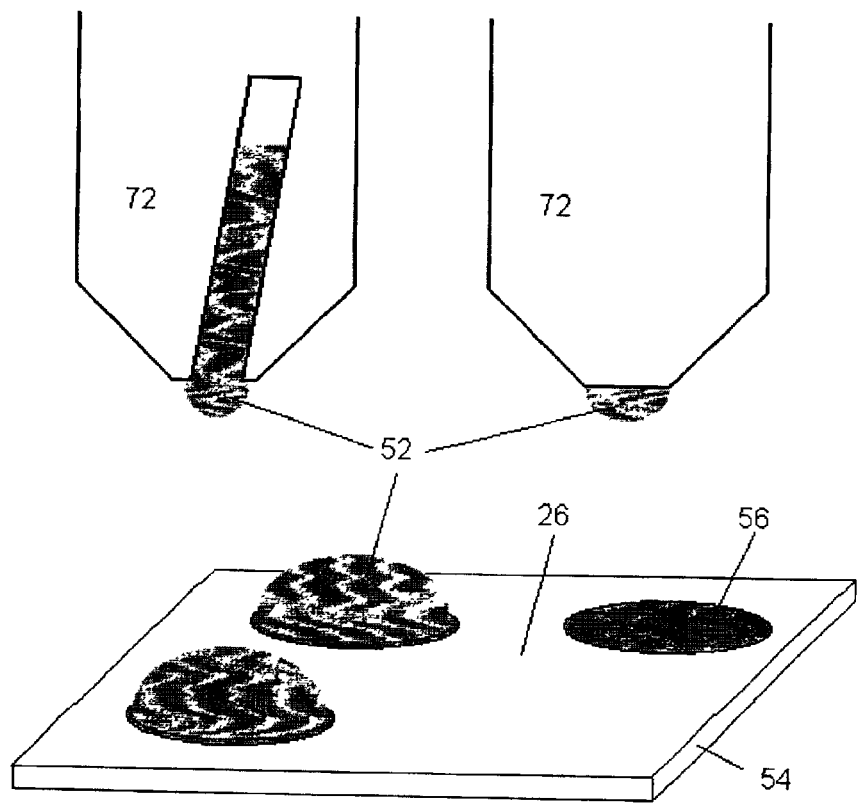

FIG. 22 illustrates a contamination free pipetting method for direct carrier and compound application using disposable pipetting tips. Pipetting system based on a disposable (and thus contamination free) two-dimensional array of pipettes 72 implemented in a lid for micro-titer plates 70. In the physical dimensions appropriate for this approach, the slit in each pipette 72 (preferably made of hard plastic as a disposable) functions as a capillary canal, filling itself with liquid 52 or 36 when lowered into a liquid filled well in a micro-titer plate.

A part of the liquid picked up in such a pipette 72 can then be transferred to a carrier plate 54 containing hydrophilic regions 56 isolated by hydrophobic areas 26 (indirect compound application).

Alternatively, pipetting can be done by pipettes having a flat tip on which a droplet of liquid 52 or 36 is formed as the pipette is moved out of the liquid. The amount of liquid remaining at the pipette tip is determined by area and hydrophilic characteristics of the tip—both of which are controllable in the manufacturing process.

Another alternative is to use pipetting tips which are basically capillary canals, this approach will be described later in relation to FIGS. 24A–C.

If direct compound application is preferred, the pipettes 72 can be used to carry compounds 52 or 36 directly to a test confinement. Please refer to FIGS. 24A–C for details.

Figure 23A:
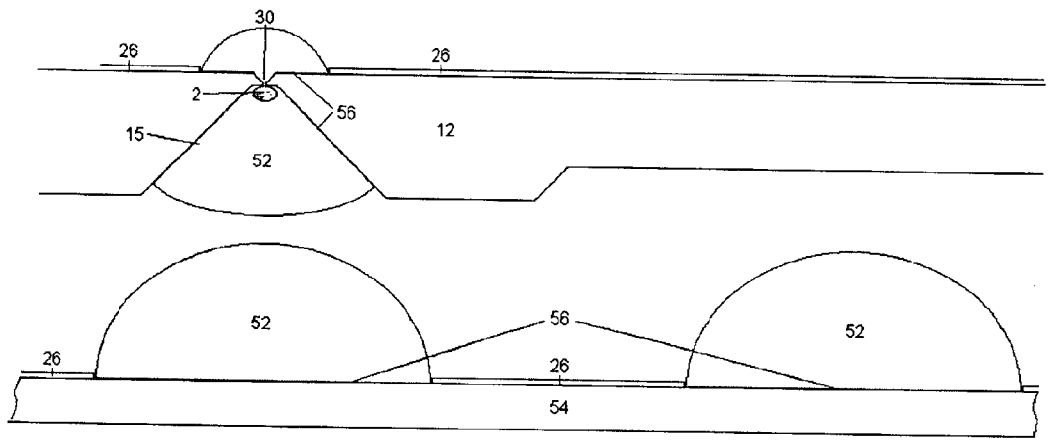

FIGS. 23A and B illustrate an embodiment of indirect compound application using a compound carrier plate. Here, compounds are first deposited on a carrier plate 54 as described in relation to direct compound application as described in relation to FIG. 22.

Figure 23B:
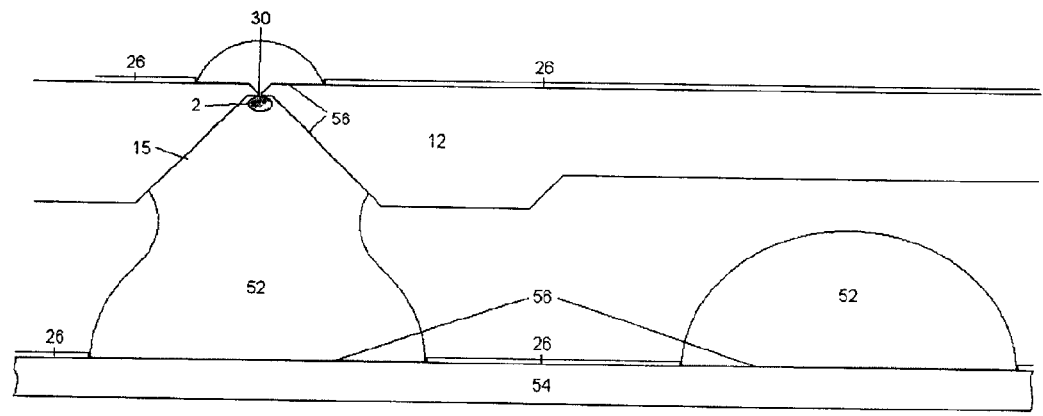

In FIG. 23A, the carrier plate 54 with the compound droplets 52 are then positioned above or below the substrate 12 containing cells 2 in carrier liquid droplets 52. The liquid exchange occurs when the drop of liquid 52 at the test confinement 15 is brought into contact with a droplet 52 on the carrier plate 54 as shown in FIG. 23B. In order to make an exchange of a sufficient amount of liquid around the cell 2, the volumes of the droplets 52 on the carrier plate 54 are assumed to be large compared to the volume of the test confinement 15. In the area around the test confinement 15, the thickness of the substrate 12 is decreased such that droplets 52 on the carrier plate 54 will not come into contact with the substrate 12 except at the position of the test confinement 15.

In FIGS. 23A and B, the carrier plate 54 is positioned below the substrate 12. The opposite situation in which the carrier plate 54 and the substrate 12 are flipped so that the droplets are applied to the test confinement 15 from above is equally valid.

FIGS. 24A–C illustrate a principle of direct compound application using pipetting tips or capillary canals of different lengths.

FIGS. 24A and B illustrate the usage of liquid exchange by capillaries 60 and 62 which are jointly mounted (ideally implemented in a lid for micro-titer plates as described in relation to FIGS. 22A and B) allowing for direct compound application. The capillaries are of different length and should be used together with a special substrate with passages 58 around the test confinement 15, as illustrated in FIG. 24C. Empty capillary canals 60, which are longer than those carrying the new compounds, are used for the removal of liquids by lowering the mount to bring a capillary canal 60 in contact with the liquid to be removed. The compound carrying capillary canals 62 are shorter than the empty capillary canals 60 such that the liquids at the tip of the filled canals will not come into contact with the substrate. In order to carry new compounds to the test confinement, the mount is moved so that the filled capillary canal 62 is above the test confinement 15. By lowering the mount, the liquid from the filled capillary canal 62 will be deposited at the site. At this point, the longer capillary canal 60 lowers into a passage 58 as shown in FIG. 24C.

FIG. 24B is a side view of the capillaries 60 and 62 ideally implemented in a lid 70 for micro-titer plates as described for FIGS. 22A and B). FIG. 24C is a top view of a complete test position containing the test confinement 15, contacts 20 to the amplifier electronics and perforations 58.

The application of compounds as described in the above can be carried out by using either standard robotics equipment for HTS-systems, or by using special-built application systems based on existing technologies such as inc-jet or bubble jet valves as found in printer heads.

Alternatively, a custom-designed lid for micro-titer plates containing integrated pipettes can be used, either for indirect pipetting or for direct compound application—this will ensure contamination free pipetting. Yet an alternatively is to use a new application system designed using chip technology.

Using the compound application systems described before, test compounds can be applied either as liquid streams, as droplets or as sprays. The advantage of the first two methods as opposed to the latter, is that an applied (reference or test) compound can largely be removed before applying a different compound.

If the test confinements are accessible from above, droplets of supporting liquid and cells can be supplied at each test confinement by the dispensing or pipetting system as described in the previous sections. Alternatively, systems such as an ink jet printer head or a bubble jet printer head can be used. Another possibility is an nQUAD aspirate dispenser or any other dispensing/pipetting device adapted to dose small amounts of liquid. Alternatively, supporting liquid and cells are applied on the substrate as a whole (e.g. by pouring supporting liquid containing cells over the substrate or immersing the substrate in such), thereby providing supporting liquid and cells to each test confinement. Since the volumes of supporting liquid and later test compounds are as small as nanoLiters, water vaporisation could represent a problem. Therefore, depending of the specific volumes, handling of liquids on the substrate should preferably be carried out in high humidity atmospheres.

In the following sections, a preferred system according to the present invention is described referring to the prior description of embodiments of individual parts of the system. The description will be given as a procedure for establishing an applicable measuring configuration.

The procedure applies a substrate according to the embodiment described in relation to FIGS. 2A–C, the substrate comprises a plurality of equivalent sites, however, this description will be given for one site only.

Liquid Loading

Put a droplet of ion-containing liquid on top of the inlet 44. The droplet on the inlet 44 now flows through the canal 32 to the outlet 46 by capillary force or external pressure such that electrical contact (via the ion-containing liquid) is established between the working electrode 16 and the electrodes 6. Then apply a voltage between the working electrode 16 and the electrodes 6 such that a flow and/or positive pressure is generated at the bottom of the passage 30, thus pushing a small amount of liquid through the passage 30 to the bottom of the well. Now put a droplet of an ion-containing liquid (ringer) in the well. Liquid contact between the liquid in the well and in the canal 32 is established when the liquid in the well reaches the bottom of the well. This liquid contact establishes electrical contact (via ion-containing liquids) between the reference electrode 8 and the working electrode 16.

Alternatively, first a droplet of an ion-containing liquid (ringer) is put in the well. Then a droplet of ion-containing liquid is put on top of the inlet 44. The droplet on the inlet 44 now flows through the canal 32 to the outlet 46 by capillary force or external pressure such that electrical contact (via the ion-containing liquid) is established between the working electrode 16 and the electrodes 6. While flowing through the canal 32, the flow of the liquid generates a negative pressure (suction) at the bottom of the passage 30, thus aiding in the establishment of liquid contact between the liquid in the well and in the canal 32. This liquid contact establishes electrical contact (via ion-containing liquids) between the reference electrode 8 and the working electrode 16. If liquid contact is not established spontaneously, a voltage can be applied between the working electrode 16 and the electrodes 6 such that a flow and/or pressure is generated at the bottom of the passage 30, thus drawing a small amount of liquid through the passage 30, thereby establishing contact between the liquid in the well and the liquid in the canal 32.

Liquid Suction (Flow Via Electroosmosis)

When and electrical field is applied between the working electrode 16 and the electrodes 6 an electroosmotic flow and/or pressure occurs in the liquid in the canal 32. The flow and/or pressure of the liquid in the tubing is controlled by the voltage between the working electrode 16 and the electrodes 6 such that the liquid passing the bottom-side of the passage 30 is either moving (flow) or generating suction (pressure) on the liquid in and above the passage 30.

Cross-Hole Current Measurement

When a voltage difference is applied between the reference electrode 8 and the working electrode 16, the resulting current through the passage 30 is measured via the working electrode 16. While this process occurs, the electrode 6 must be "disabled" in a high-impedance state such that it will not introduce electrical noise.

Cell Positioning

The liquid flow through the passage 30 needed to guide the cell towards the passage on top of which it must be positioned, is generated by the liquid suction resulting from the liquid flow and/or suction in the canal 32 as described above.

Cell Adhesion and Sealing

The adhesion of a cell to the top rim of the passage 30, and the high resistance sealing of the cell membrane around the passage can be assisted by applying a negative pressure (suction) on the part of the cell membrane above the passage 30. The suction below the passage is generated by the electroosmotic flow resulting from the application of a potential between the working electrode 16 and the electrodes 6 with the reference electrode 8 in a high-impedance state.

Establishment of Whole-cell Configuration

A whole-cell measurement configuration in which the cell membrane is ruptured at the passage 30 can be established by applying an increasing suction through the passage 30. This can be done by generating an electroosmotic flow resulting from the application of a potential between the working electrode 16 and the electrodes 6 with the reference electrode in a high-impedance stage. Another way of rupturing the cell membrane at the passage 30 is by applying one or more voltage pulses between the reference electrode 8 and the working electrode 16 until the membrane is ruptured (zapping). Voltage pulses between 0.5 V and 1.0 V of duration of 10 micro-seconds to 1 second work well with many cell types. A preferred approach is to increase either the voltage or the pulse-time or both for each subsequent pulse until a capacitative spike in the recorded current indicates that the cell membrane has ruptured. During the entire process or at least between the individual voltage pulses, it is often advantageous to apply a moderate negative pressure on the cell membrane through the passage 30 to avoid that the ruptured cell re-seals, and to ensure that the cell does not become leaky. The cross-membrane potential is applied between the working electrode 16 and the reference electrode 8 with the electrode 6 in a high-impedance state. The suction below the passage is generated by the electroosmotic flow resulting from the application of a potential between the working electrode 16 and the electrode 6 with the reference electrode 8 in a high-impedance state.

Exchange of Compounds

Compounds can be applied by the droplet or "pipette" method described elsewhere.

At the present stage, a substrate with some electrodes each holding a cell is provided, the chosen cells form a giga-seal around their respective electrodes, allowing for the electrode to measure electrophysiological properties of the ion transfer channels in the cell membrane. This represents the main aspect of the invention, the making available of a plurality of prepared sample cells for performing electrophysiological experiments. Moreover, each cell is confined in order to permit individual testing of cells. The remaining of the description will focus on the applications of the prepared substrate.

The test compounds have to be added to each test confinement individually, with different test compounds for each test confinement. This can be carried out using the methods for applying supporting liquid, with the exception of the methods where supporting liquid are applied on the substrate as a whole.

Having positioned the cell in a measuring configuration, several electrophysiological properties can be measured, such as current through ion channels (voltage clamp), electric potential drop across ion channels (current clamp), or capacitance of ion channel-containing membranes. In any case, a specific electronic measuring circuit should be provided. One such possible circuit for voltage clamp measurements is described in the prior art with reference to FIGS. 15 to 20.

In the case of voltage clamp measurements, the electrical current $I_{mem}$ carried by the ion transfer channels in the cell membrane results in a charge transfer from the solution (reference electrode) to the working electrode, typically of the order of pA to $\mu$A (picoampere—$10^{-12}$ A). The potential drop over the membrane in the measuring configuration is $V_{mem}$.

The following is a shorthand description of a preferred procedure for preparing and performing a patch clamp experiment according to the present invention.

1. Test media preparation
    Fetch from storage (and fill with physiological buffer solution)
2. Pipetting preparation
    Using disposable array-pipettes: fetch disposable array-pipette and droplet-carrier from storage
    Not using disposable array-pipette: wash array pipette
3. Compound preparation
    Fetch compounds from storage (in micro-titer plates)
    Using direct pipetting: load pipettes with test compounds
    Using indirect-pipetting: perform pipetting of test-, wash- and control-compounds to carrier
4. Cells in suspension
    From incubator with $CO_2$ and temperature control
5. Cell sorting
    Through magnetic or mechanical filter
6. Cell application
    On fresh, test media (with physiological buffer solution)
7. Cell positioning
    Electroosmosis, convection, gravity, liquid flow (generated by electroosmosis, capillary action or osmosis) all possibly combined with appropriate geometric coatings
8. Cell adhesion
    As for cell positioning, possibly combined with lipid contacts
9. Cell giga-sealing (via $R_{mem}=V_{mem}/I_{mem}$)
    As for Cell adhesion
10. Establishment of whole-cell (via Capacitative spike on $I_{mem}$)
    Suction (generated by electroosmosis), zapping, or pore forming compound 11. Baseline check (via set $V_{mem}$, $I_{mem}$ traces vs. time are analysed)
    Control against run-down
12. Test-compound application
    Direct or indirect pipetting using droplets or by tubing integrated in the test media
13. Voltage-Clamp recordings (via set $V_{mem}$, record $I_{mem}$ traces vs. time)
14. Compound wash-off
    As for Test-compound application
15. Reference-compound application
    As for Test-compound application
16. Voltage-Clamp recordings (for control purposes)
17. Disposing of test media
18. Next experiment The following presents details to the performance of each step of the procedure with references in brackets [ ] to the system overview shown in FIG. 21.

Steps 1–3 can advantageously be performed by using commercially available robotics systems optimised for general HTS. One such well suited system is the Tecan Genesis RMP (Robotic Microplate Processor) system, e.g. the Tecan Genesis RMP 300 [304, 310, 340, 342], or a larger workstation system based on one of these, equipped with a liquid handling arm [320, 324](used for pipetting) and a Robotic Manipulator Arm (RoMa) [322] for transport of test media, disposable pipettes, microplates and reagent racks to all positions of the RMP. The Tecan Genesis RMP with connected robot arms can be controlled by Tecan's GEMINI software.

If non-disposable pipettes (single or array) are being used, the Tecan Genesis RMP can be equipped with a Washer system, and in the case of array pipettes, the pipetting system can be the Tecan Genesis RWS Multichannel Pipetting option, allowing for 500 nl–200 ml pipetting. In case of a 1–8 pipetting system, the Tecan Genesis NPS nano-pipetting system can be used, allowing for 10 nl–5 ml pipetting.

For compound storage, one or more Tecan Mol Bank [334] can be integrated, each allowing for up to 2500 microtiter plates containing test compounds to be registered (using bar-codes), stored and retrieved upon demand. One or more Mol Bank units can be controlled by Tecan's FACTS software.

Steps 4–5 can be performed using one or more custom built devices or alternatively by using commercially available devices.

The Tecan Incubator/Shaker [330] can be used for incubation of cells in a $CO_2$ and temperature controlled environment. The Tecan Te-MagS Magnetic Bead Separation unit may be integrated into the system and used for cell separation. The Te-MagS can be controlled by Tecan's GEMINI software.

6–8 can be performed using a custom-built device [350].

9–17 will be performed in a custom built device [360] integrating a holding device for the test media, the stimulation and recording electronics and a device for compound application in the case of indirect compound application.

Alternatively, if direct compound application using an array pipetting system is being used, the custom built device will contain one or more openings through which the test-, wash- and control compounds can be applied by the external pipetting system.

12–14 may be repeated numerous times if more than one test-compound is tested per cell.

The throughput of the system depends on the number of times a giga-sealed cell can be used with different compounds.

One Compound Per Cell System

| | |
|---|---|
| Media exchange and initial loading | app. 2 min |
| Cell positioning, giga-sealing, establishment of whole-cell configuration, baseline check | app. 5 min |
| Application of test-compound and data collection | app. 2 min |
| Wash-off of test-compound | app. 1 min |
| Application of reference-compound and data collection | app. 1 min |
| Complete cycle-time | app. 11 min |

Assuming a 50% success rate this gives a capability of testing app. 60 compounds per day on each "test-site". Simultaneous handling of 96 "test-sites" allows for the testing of app. 5.000 compounds per day. Simultaneous handling of 384 "test-sites" allows for the testing of app. 20.000 compounds per day.

Four Compounds Per Cell System

| | |
|---|---|
| Media exchange and initial loading | app. 2 min |
| Cell positioning, giga-sealing, establishment of whole-cell configuration, baseline check | app. 5 min |
| Four times application of test-compound and data collection | app. 8 min |
| Four times wash-off of test-compound | app. 4 min |
| Application of reference-compound and data collection | app. 1 min |
| Complete cycle-time | app. 20 min |

Assuming a 50% success rate this gives a capability of testing app. 144 compounds per day on each "test-site". Simultaneous handling of 96 "test-sites" allows for the testing of app. 12.500 compounds per day. Simultaneous handling of 384 "test-sites" allows for the testing of app. 50.000 compounds per day.

What is claimed is:

1. A system for determination and/or monitoring of electrophysiological properties of ion channels in ion channel-containing lipid membranes, the system comprising a substrate comprising a plurality of sites for holding ion channel-containing lipid membranes, a plurality of working electrodes, one working electrode positioned at each site, and one or more reference electrodes positioned so as for each site to be in electrical contact with at least one reference electrode, each site being adapted to hold an ion channel-containing lipid membrane so as for an electrical current $I_{mem}$ drawn between the working electrode of a site and a reference electrode will be transmitted by ion channels in the ion channel-containing lipid membrane, the system further comprising a main electric circuit for performing voltage clamp measurements on ion channel-containing lipid membranes held at the sites, said main electric circuit comprising
   a plurality of current to voltage (I-V) converters, wherein the I-V converters comprise an operational amplifier and a dual FET, and each having a first and a second input and an output, the first input being electrically connected to a working electrode and the second input receiving a reference potential $V_{ref}$, each I-V converter being adapted to, upon receiving the reference potential $V_{ref}$, draw a current $I_{mem}$ between a reference electrode and the working electrode until the potential on the first input at least substantially equals $V_{ref}$, each I-V converter further being adapted to provide on its output a first voltage signal corresponding to $I_{mem}$,
   a first multiplexer having a plurality of inputs for receiving first voltage signals from two or more I-V converters and individually feeding the selected first voltage signals to a first A/D converter in a controlled manner, said first A/D converter to generate digital signals corresponding to the first voltage signals, digital processing means for receiving and processing the digital signals, the digital processing means being adapted to administer and generate a first type of digital signals related to stimulation or testing of the ion channel-containing lipid membranes, the digital processing means further being adapted to administer and generate a second type of digital signals controlling individually controllable components of the main circuit, means for receiving the digital signals of the first type and for generating an analogue stimulation or testing signal $V_{stim}$ to be added to each $V_{ref}$, wherein the means for generating $V_{stim}$ further comprises a plurality of digital to analogue (D-A) converters for receiving the digital signals of the first type and providing a corresponding analogue signal $V_{stim}$ and a plurality of multiplexers each connected to a D/A converter for receiving the analogue signals of the first type, and a plurality of individually controllable sample and hold circuits, where two or more sample and hold circuits are connected to different outputs from each multiplexer, the means for generating $V_{stim}$ being adapted to provide a real time ramped $V_{stim}$ signal consisting of a two or more parts, each part corresponding to a digital signal of the first type, in that the D/A converters are adapted to generate a first analogue signal in response to a first digital signal of the first type and a second analogue signal in response to a second digital signal of the first type, the multiplexer is adapted to provide the first analogue signal on a first output and the second analogue signal on a second output, the individually controllable sample and hold circuits is adapted to receive and hold said first and second analogue signals until controlled to sequentially release the analogue signals so as to form different parts of a ramped $V_{stim}$ signal means for providing $V_{ref}$ to each I-V converter, each $V_{ref}$ being individually controllable, said means further being adapted to receive $V_{stim}$ and add $V_{stim}$ to one or more selected $V_{ref}$'s, and an enable network for receiving the digital signals of the second type from the digital processing means and for controlling:

the plurality of individually controllable switches, the selection of the plurality of first voltage signals in the multiplexer, the value of individual $V_{ref}$'s by controlling the means for providing $V_{ref}$, in response to the digital signals of the second type.

2. A system according to claim 1, wherein the individually controllable switches are integrated on the substrate.

3. A system for determination and/or monitoring of electrophysiological properties of ion channels in cells, said system comprising:

a cell incubation unit, a compound storage unit, one or more substrates for determination and/or monitoring of electrophysiological properties of ion channels in ion channel-containing lipid membranes, said substrate comprising:

a first site for holding ion channel-containing lipid membranes, the site comprising a passage in the substrate, a first end of the passage being in contact with a first domain at a first upper surface part of the substrate and a second end of the passage being in contact with a second domain in a first canal, a reference electrode in electrical contact with the first domain, a working electrode in electrical contact with the second domain, one or more electrodes for generating a first electrical field in the first canal, the further electrodes having dimensions and positions so as for the first electrical field to induce a flow in an ionic solution held in the first canal, the second end of the passage and the first canal being dimensioned so that a flow of an ionic solution in the first canal can generate a flow through the passage from the first domain into the second domain or vice versa, and the first end part of the passage being adapted to form a seal with an ion channel-containing lipid membrane held at the site, the substrate, the seal and the lipid membrane thereby separating the first domain of the site from the second domain so that one or more electrical properties of the membrane can be determined and/or monitored by determining and/or monitoring an electrical signal between the reference electrode and the working electrode a substrate storage unit, a cell positioning and measurement unit for receiving a substrate, said cell positioning and measurement unit comprising means for applying a cell containing liquid to each site of a substrate, means for applying a predetermined potential difference between a predetermined set of electrodes at each site of the substrate in order to position cells at predetermined positions at the sites, and a main electronic circuit according to claim 1 for performing testing and measurements of positioned cells, transportation means for transporting substrates from the substrate storage unit to the cell positioning and measurement unit, the transportation means further being adapted to transport cells from the cell incubation unit to the cell positioning and measurement unit, a pipetting system for pipetting compounds from the compound storage unit to a substrate held in the cell positioning and measurement unit, a main computer system for controlling execution of the determination and/or monitoring and for storage of experiment data, said main computer being operationally connected to the one or more electronic processors for data acquisition and analysis, said one or more electronic processors being operationally connected to the digital processing means of the main electronic circuit of the cell positioning and measurement unit, electronic processor means for controlling the transportation means, electronic processor means for controlling the pipetting system.

4. A system according to claim 1, wherein said main electric current further comprises a plurality of individually controllable switches, each being operationally connected to a working electrode and the multiplexer, for switching the first voltage signal to the multiplexer on or off.

5. A system for determination and/or monitoring of electrophysiological properties of ion channels in ion channel-containing lipid membranes, the system comprising a substrate comprising a plurality of sites for holding ion channel-containing lipid membranes, a plurality of working electrodes, one working electrode positioned at each site, and one or more reference electrodes positioned so as for each site to be in electrical contact with at least one reference electrode, each site being adapted to hold an ion channel-containing lipid membrane so as for an electrical current $I_{mem}$ drawn between the working electrode of a site and a reference electrode will be transmitted by ion channels in the ion channel-containing lipid membrane, the system further comprising a main electric circuit for performing voltage clamp measurements on ion channel-containing lipid membranes held at the sites, said main electric circuit comprising a plurality of current to voltage (I-V) converters, wherein the I-V converters comprise an operational amplifier and a dual FET, and each having a first and a second input and an output, the first input being electrically connected to a working electrode and the second input receiving a reference potential $V_{ref}$, each I-V converter being adapted to, upon receiving the reference potential $V_{ref}$, draw a current $I_{mem}$ between a reference electrode and the working electrode until the potential on the first input at least substantially equals $V_{ref}$, each I-V converter further being adapted to provide on its output a first voltage signal corresponding to $I_{mem}$, a first multiplexer having a plurality of inputs for receiving first voltage signals from two or more I-V converters and individually feeding the selected first voltage signals to a first A/D converter in a controlled manner, said first A/D converter to generate digital signals corresponding to the first voltage signals, a plurality of individually controllable switches, each being operationally connected to a working electrode and the multiplexer, for switching the first voltage signal to the multiplexer on or off, digital processing means for receiving and processing the digital signals, the digital processing means being adapted to administer and generate a first type of digital signals related to stimulation or testing of the ion channel-containing lipid membranes, the digital processing means further being adapted to administer and generate a second type of digital signals controlling individually controllable components of the main circuit, means for receiving the digital signals of the first type and for generating an analogue stimulation or testing signal $V_{stim}$ to be added to each $V_{ref}$, wherein the means for generating $V_{stim}$ further comprises a plurality of digital to analogue (D-A) converters for receiving the digital signals of the first type and providing a corresponding analogue signal $V_{stim}$ and a plurality of multiplexers each connected to a D/A converter for receiving the analogue signals of the first type, and a plurality of individually controllable sample and hold circuits, where two or more sample and hold circuits are connected to different outputs from each multiplexer, the means for generating $V_{stim}$ being adapted to provide a real time ramped $V_{stim}$ signal consisting of a two or more parts, each part corresponding to a digital signal of the first type, in that the D/A converters are adapted to generate a first analogue signal in response to a first digital signal of the first type and a second analogue signal in response to a second digital signal of the first type, the multiplexer is adapted to provide the first analogue signal on a first output and the second analogue signal on a second output, the individually controllable sample and hold circuits is adapted to receive and hold said first and second analogue signals until controlled to sequentially release the analogue signals so as to form different parts of a ramped $V_{stim}$ signal means for providing Vref to each I-V converter, each $V_{ref}$ being individually controllable, said means further being adapted to receive $V_{stim}$ and add $V_{stim}$ to one or more selected $V_{ref}$'s, and an enable network for receiving the digital signals of the second type from the digital processing means and for controlling:
  the plurality of individually controllable switches,
  the selection of the plurality of first voltage signals in the multiplexer,
  the value of individual $V_{ref}$'s by controlling the means for providing $V_{ref}$ in response to the digital signals of the second type.

6. A system according to claim 2 or 5, wherein at least part of each I-V converter is integrated on the substrate.

* * * * *